United States Patent
Jhiang et al.

(10) Patent No.: US 11,790,524 B2
(45) Date of Patent: Oct. 17, 2023

(54) SYSTEM AND METHOD FOR QUANTITATIVE VOLUMETRIC ASSESSMENT AND MODELING OF TUMOR LESIONS

(71) Applicant: Ohio State Innovation Foundation, Columbus, OH (US)

(72) Inventors: Sissy M. Jhiang, Columbus, OH (US); Chia-Hsiang Menq, Columbus, OH (US); Peng Cheng, Westerville, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 8 days.

(21) Appl. No.: 16/903,911

(22) Filed: Jun. 17, 2020

(65) Prior Publication Data
US 2020/0402231 A1    Dec. 24, 2020

Related U.S. Application Data

(60) Provisional application No. 62/864,258, filed on Jun. 20, 2019.

(51) Int. Cl.
*G06T 7/00* (2017.01)
*G06T 7/11* (2017.01)
(Continued)

(52) U.S. Cl.
CPC .......... *G06T 7/0012* (2013.01); *A61B 5/4842* (2013.01); *G06T 7/11* (2017.01); *G06T 7/30* (2017.01); *G06T 2207/10081* (2013.01); *G06T 2207/10088* (2013.01); *G06T 2207/10104* (2013.01); *G06T 2207/10108* (2013.01);
(Continued)

(58) Field of Classification Search
CPC ... G06T 7/11; G06T 7/30; G06T 2207/10081; G06T 2207/30061; G06T 2207/10104; G06T 2207/10108; G06T 2207/10088; G06T 2207/30096; G06T 7/136; G06T 7/155; G06T 7/0016; A61B 5/4842; A61B 5/0073; A61B 5/0033; A61B 5/004
See application file for complete search history.

(56) References Cited

U.S. PATENT DOCUMENTS

2010/0250275 A1\*  9/2010  Sakagawa ................ A61B 6/00
                                                                        705/2
2019/0066294 A1\*  2/2019  Yu .......................... G06T 7/143
(Continued)

OTHER PUBLICATIONS

Sun, Shanhui, Christian Bauer, and Reinhard Beichel. "Automated 3-D segmentation of lungs with lung cancer in CT data using a novel robust active shape model approach." IEEE transactions on medical imaging 31.2 (2011): 449-460 . . . https://ieeexplore.ieee.org/document/60423 (Year: 2011).\*

(Continued)

*Primary Examiner* — John Villecco
*Assistant Examiner* — Han Hoang
(74) *Attorney, Agent, or Firm* — Meunier Carlin & Curfman LLC

(57) ABSTRACT

Disclosed are systems, methods, and computer program products for tumor lesion identification, segmentation, tracking and analysis, wherein a 3D spatial distribution of the tumor lesions in a target organ forms a unique 3D point structure for a patient.

15 Claims, 18 Drawing Sheets

(51) Int. Cl.
  *G06T 7/30* (2017.01)
  *A61B 5/00* (2006.01)
(52) U.S. Cl.
  CPC ............... *G06T 2207/30061* (2013.01); *G06T 2207/30096* (2013.01)

(56) References Cited

U.S. PATENT DOCUMENTS

2020/0352998 A1* 11/2020 Albertson ........ G01N 33/57407
2021/0106208 A1*  4/2021 Iwaki ............... A61B 1/000094

OTHER PUBLICATIONS

G. J. Kemerink, R. J. Lamers, B. J. Pellis, H. H. Kruize, J. M. A. van Engelshoven, "On segmentation of lung parenchyma in quantitative computed tomography of the lung," Medical Physics, vol. 25, No. 12, pp. 2432-2439, 1998.
S. Hu, E. A. Hoffman, J. M. Reinhardt, "Automatic lung segmentation for accurate quantitation of volumetric X-ray CT images," IEEE Transactions on Medical Imaging, vol. 20, No. 6, pp. 490-498, 2001.
Y. Itai, H. Kim, S. Ishikawa et al., "Automatic segmentation of lung areas based on SNAKES and extraction of abnormal areas," in Proceedings of the 17th IEEE International Conference on Tools with Artificial Intelligence (ICTAI '05), pp. 377-381, 2005.
M. Silveira, J. Nascimento, and J.Marques, "Automatic segmentation of the lungs using robust level sets," in Proceedings of the 29th IEEE Annual International Conference of Medicine and Biology Society (EMBS '07), pp. 4414-4417, 2007.
I. Sluimer, M. Prokop, and B. Van Ginneken, "Toward automated segmentation of the pathological lung in CT," IEEE Transactions on Medical Imaging, vol. 24, No. 8, pp. 1025-1038, 2005.
M. Sofka, J. Wetzl, N. Birkbeck et al., "Multi-stage learning for robust lung segmentation in challenging CT volumes," in Proceedings of the International Conference on Medical 27 Imaging Computing and Computer-Assisted Intervention (MICCAI '11), pp. 667-674, 2011.
S. Sun, C. Bauer, and R. Beichel, "Automated 3D segmentation of lungs with lung cancer in CT data using a novel robust active shape model approach," IEEE Transactions on Medical Imaging, vol. 31, No. 2, pp. 449-460, 2012.
A. M. Mendonca, J. A. da Silva, and A. Campilho, "Automatic delimitation of lung fields on chest radiographs," in Proceedings of the International Symposium on Biomedical Imaging (ISBI '04), vol. 2, pp. 1287-1290, 2004.
P. Campadelli, E. Casiraghi, and D. Artioli, "A fully automated method for lung nodule detection from postero-anterior chest radiographs," IEEE Transactions on Medical Imaging, vol. 25, No. 12, pp. 1588-1603, 2006.
P. Korfiatis, S. Skiadopoulos, P. Sakellaropoulos, C. Kalogeropoulou, and L. Costaridou, "Combining 2D wavelet edge highlighting and 3D thresholding for lung segmentation in thin-slice CT," British Journal of Radiology, vol. 80, No. 960, pp. 996-1005, 2007.
A. Mansoor, U. Bagci, Z. Xu, "A generic approach to pathological lung segmentation," IEEE Transactions on Medical Imaging, vol. 33, No. 12, pp. 2293-2310, 2014.
J. Yao, A. Dwyer, R.M. Summers, D.J. Mollura, "Computer-aided diagnosis of pulmonary infections using texture analysis and support vector machine classification," Academic Radiology., vol. 18, No. 3, pp. 306-314, 2011.
E. M. van Rikxoort, and B. van Ginneken, "Automated segmentation of pulmonary structures in thoracic computed tomography scans: a review," Physics in Medicine & Biology, vol. 58, No. 17, pp. R187-R220, 2013.
A. Mansoor, U. Bagci, B. Foster, Z. Xu, G. Z. Papadakis, L. R. Folio, F. K. Udupa, D. F. Mollura, "Segmentation and image analysis of abnormal lungs at CT: Current approaches, challenges, and future trends," RadioGraphics, vol. 35, No. 4, pp. 1056-1076, 2015.
S. G. Armato, M. L. Giger, C. J. Moran, J. T. Blackburn, K. Doi, and H. MacMahon, "Computerized detection of pulmonary nodules on CT scans," Radiographics, vol. 19, No. 5, pp. 1303-1311, 1999.
Q. Wei, Y. Hu, G. Gelfand, and J. H. MacGregor, "Segmentation of lung lobes in high-resolution isotropic CT images," IEEE Transactions on Biomedical Engineering, vol. 56, No. 5, pp. 1383-1393, 2009.
A. El-Baz, G. M. Beache, G. Gimel'farb, K. Suzuki, K. Okada, A. Elnakib, A. Soliman, and B. Abdollahi, "Computer-Aided Diagnosis Systems for Lung Cancer: Challenges and Methodologies," International Journal of Biomedical Imaging, vol. 2013, 942353, 2013.
T. Matsumoto, H. Yoshimura, K. Doi et al., "Image feature analysis of falsepositive diagnoses produced by automated detection of lung nodules," Investigative Radiology, vol. 27, No. 8, pp. 587-597, 1992.
A. A. Enquobahrie, A. P. Reeves, D. F. Yankelevitz, and C. I. Henschke, "Automated detection of pulmonary nodules from whole lung helical CT scans: performance comparison for isolated and attached nodules," in Progress in Biomedical Optics and Imaging—Medical Imaging: Imaging Processing, Proceedings of SPIE, pp. 791-800, 2004.
Y. Lee, T. Hara, H. Fujita, S. Itoh, and T. Ishigaki, "Automated detection of pulmonary nodules in helical CT images based on an improved templatematching technique," IEEE Transactions on Medical Imaging, vol. 20, No. 7, pp. 595-604, 2001.
R. Wiemker, P. Rogalla, A. Zwartkruis, and T. Blaffert, "Computer aided lung nodule detection on high resolution CT data," in Medical Imaging: Image Processing, vol. 4684 of Proceedings of SPIE, pp. 677-688, 2002.
T. Ezoe, H. Takizawa, S. Yamamoto et al., "An automatic detection method of lung cancers including ground glass opacities from chest X-ray CT images," in Medical Imaging: Image Processing, vol. 4684 of Proceedings of SPIE, pp. 1672-1680, 2002.
K. Awai, K. Murao, A. Ozawa, M. Komi, H. Hayakawa, S. Hori, Y. Nishimura, "Pulmonary nodules at chest CT: effect of computer-aided diagnosis on radiologists' detection performance," Radiology, vol. 230, No. 2, pp. 347-352, 2004. Abstract only.
K. Kanazawa, Y. Kawata, N. Niki et al., "Computer-aided diagnosis for pulmonary nodules based on helical CT images," Computerized Medical Imaging and Graphics, vol. 22, No. 2, pp. 157-167, 1998.
M. N. Gurcan, B. Sahiner, N. Petrick, H. Chan, E. A. Kazerooni, P. Cascade, L. M. Hadjiiski, "Lung nodule detection on thoracic computed tomography images: preliminary evaluation of a computer-aided diagnosis system," Medical Physics, vol. 29, No. 11, pp. 2552-2558, 2002.
M. Tanino, H. Takizawa, S. Yamamoto, T. Matsumoto, Y. Tateno, and T. Iinuma, "A detection method of ground glass opacities in chest X-ray CT images using automatic clustering techniques," in Medical Imaging: Image Processing, vol. 5032 of Proceedings of SPIE, pp. 1728-1737, 2003.
J. P. Ko and M. Betke, "Chest CT: automated nodule detection and assessment of change over time—preliminary experience," Radiology, vol. 218, No. 1, pp. 267 273, 2001.
B. Zhao, M. S. Ginsberg, R. A. Lefkowitz, L. Jiang, C. Cooper, and L.H. Schwartz, "Application of the LDMalgorithmto identify small lung nodules on low-dose MSCT scans," in Proceedings of the Progress in Biomedical Optics and Imaging—Medical Imaging 2004: Imaging Processing, pp. 818-823, 2004.
E. J. Candes, X. Li, Y. Ma, J. Wright, "Robust principal component analysis?" Journal of the ACM, vol. 58, No. 3, pp. 1-37, 2011.
D. F. Yankelevitz, A. P. Reeves, W. J. Kostis, B. Zhao, and C. I. Henschke, "Small pulmonary nodules: volumetrically determined growth rates based on CT evaluation," Radiology, vol. 217, No. 1, pp. 251-256, 2000. Abstract only.
J. P. Ko, H. Rusinek, E. L. Jacobs et al., "Small pulmonary nodules: volume measurement at chest CT—phantom study," Radiology, vol. 228, No. 3, pp. 864-870, 2003.

(56) References Cited

OTHER PUBLICATIONS

W. Mullally, M. Betke, J. Wang, and J. P. Ko, "Segmentation of nodules on chest computed tomography for growth assessment," Medical Physics, vol. 31, No. 4, pp. 839-848, 2004.
W. J. Kostis, A. P. Reeves, D. F. Yankelevitz, and C. I. Henschke, "Threedimensional segmentation and growth-rate estimation of small pulmonary nodules in helical CT images," IEEE Transactions on Medical Imaging, vol. 22, No. 10, pp. 1259-1274, 2003.
W. J. Kostis, D. F. Yankelevitz, A. P. Reeves, S. C. Fluture, and C. I. Henschke, "Small pulmonary nodules, reproducibility of three-dimensional volumetric measurement and estimation of time to follow-up CT," Radiology, vol. 231, No. 2, pp. 446-452, 2004. Abstract only.
J. M. Kuhnigk, V. Dicken, L. Bornemann et al., "Morphological segmentation and partial volume analysis for volumetry of solid pulmonary lesions in thoracic CT scans," IEEE Transactions on Medical Imaging, vol. 25, No. 4, pp. 417-434, 2006.
S. A. Hijjatoleslami, J. Kittler, "Region growing: A new approach", IEEE Transactions on Image Processing, vol. 7, pp. 1079-1084, 1998.
J. Dehmeshki, H. Amin, M. Valdivieso, and X. Ye, "Segmentation of pulmonary nodules in thoracic CT scans: a region growing approach," IEEE Transactions on Medical Imaging, vol. 27, No. 4, pp. 467-480, 2008.
S. Diciotti, G. Picozzi, M. Falchini, M.Mascalchi, N. Villari, and G. Valli, "3D segmentation algorithm of small lung nodules in spiral CT images," IEEE Transactions on Information Technology in Biomedicine, vol. 12, No. 1, pp. 7-19, 2008.
T. Kubota, A. K. Jerebko, M. Dewan, M. Salganicoff, and A. Krishnan, "Segmentation of pulmonary nodules of various densities with morphological approaches and convexity models," Medical Image Analysis, vol. 15, No. 1, pp. 133-154, 2011.
Y. Kawata, N. Niki, H. Ohmatsu, and N. Moriyama, "A deformable surface model based on boundary and region information for pulmonary nodule segmentation from 3D thoracic CT images," IEICE Transactions on Information and Systems, vol. 86, No. 9, pp. 1921-1930, 2003. Abstract only.
T. W. Way, L. M. Hadjiiski, B. Sahiner et al., "Computer-aided diagnosis of pulmonary nodules on CT scans: segmentation and classification using 3D active contours," Medical Physics, vol. 33, No. 7, pp. 2323-2337, 2006.
Y. Yoo, H. Shim, I. D. Yun, K. W. Lee, and S. U. Lee, "Segmentation of ground glass opacities by asymmetric multi-phase deformable model," in Medical Imaging: Image Processing, vol. 6144, Feb. 2006.
L. R. Goodman, M. Gulsun, L. Washington, P. G. Nagy, and K. L. Piacsek, "Inherent variability of CT lung nodule measurements in vivo using semiautomated volumetric measurements," American Journal of Roentgenology, vol. 186, No. 4, pp. 989-994, 2006.
J. H. Moltz, M. Schwier, H. Peitgen, "A general framework for automatic detection of matching lesions in follow-up CT," 2009 IEEE International Symposium on Biomedical Imaging: From Nano to Macro, pp. 843-846, 2009.
A. Sotiras, C. Davatzikos, and N. Paragios, "Deformable Medical Image Registration: A Survey," IEEE Trans Med Imaging, vol. 32, No. 7, pp. 1153-1190, 2013.
A. Myronenko, X. Song, "Point set registration: coherent point drift," IEEE Transactions on Pattern Analysis and Machine Intelligence, vol. 12, pp. 2262-2275, 2010.
J. J. Erasmus, G. W. Gladish , L. Broemeling , B. S. Sabloff, M. T. Truong , R. S. Herbst, R. F. Munden, "Interobserver and Intraobserver Variability in Measurement of Non-Small-Cell Carcinoma Lung Lesions: Implications for Assessment of Tumor Response," Journal of Clinical Oncology, vol. 21, No. 13, pp. 2574-2582, 2003.
J. Egger, T. Kapur, A. Fedorov, S. Pieper, J. V. Miller, H. Veeraraghavan, B. Freisleben, A. J. Golby, C. Nimsky, R. Kikinis, "GBM Volumetry using the 3D Slicer Medical Image Computing Platform," Scientific Reports, vol. 3, pp. 1364, 2013.
B. Gaonkar, L. Macyszyn, M. Bilello, M. S. Sadaghiani, H. Akbari, M. A. Atthiah, Z. S. Ali, X. Da, Y. Zhan, D. O'Rourke, S. M. Grady, and C. Davatzikos, "Automated tumor volumetry using computer-aided image segmentation," Academic Radiology, vol. 22, No. 5, pp. 653-661, 2015.
W. Cai, and G. Hong, "Quantitative image analysis for evaluation of tumor response in clinical oncology," Chronic diseases and translational medicine, vol. 4, No. 1, 18-28, 2018.
K. A. Miles, "How to use CT texture analysis for prognostication of non-small cell lung cancer," Cancer imaging, vol. 16, 10, 2016.
B. Ganeshan, and K. A. Miles, "Quantifying tumour heterogeneity with CT," Cancer imaging, vol. 13, No. 1, pp. 140-149, 2013.
M. B. Andersen, S. W. Harders, B. Ganeshan, J. Thygesen, H. H. T. Madsen, F. Rasmussen, "CT texture analysis can help differentiate between malignant and benign lymph nodes in the mediastinum in patients suspected for lung cancer," Acta Radiologica, vol. 57, No. 6, pp. 669-676, 2016. Abstract only.
S. Wold, K. Esbensen, and P. Geladi, "Principal component analysis," Chemometrics and Intelligent Laboratory Systems, vol. 2, No. 1-3, pp. 37-52, 1987.
X. Wang, K. Mao, L. Wang, P. Yang, D. Lu, and P. He, "An Appraisal of Lung Nodules Automatic Classification Algorithms for CT Images," Sensors, vol. 19, No. 1, 194, 2019.
M. Batty, R. Morphet, P. Masucci, and K. Stanilov, "Entropy, complexity, and spatial information," J Geogr Syst, vol. 16, pp. 363-385, 2014.
E. M. Rikxoort, B. Hoop, S. Vorst, M. Prokop, and B. Ginneken, "Automatic Segmentation of Pulmonary Segments From Volumetric Chest CT Scans," IEEE Trans. on Medical Imaging, vol. 28, No. 4, pp. 621-630, 2009.

\* cited by examiner

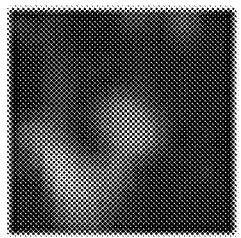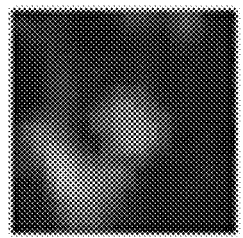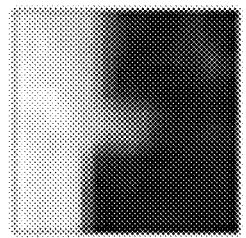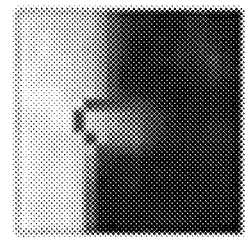
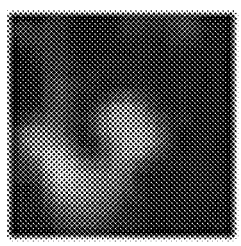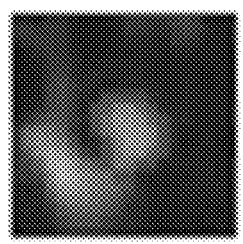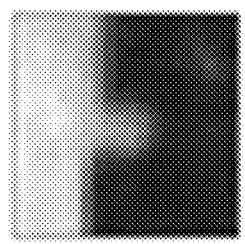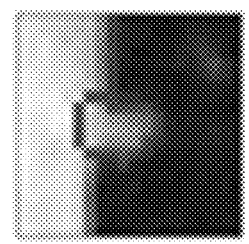
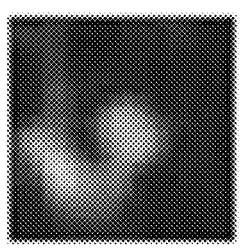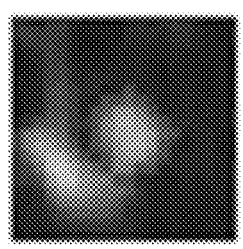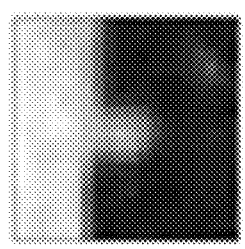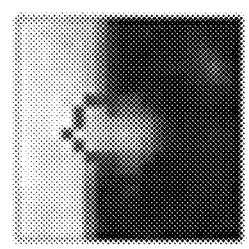
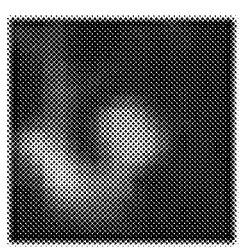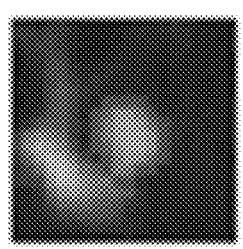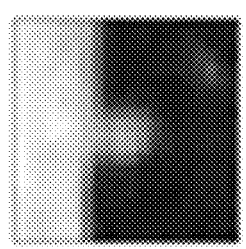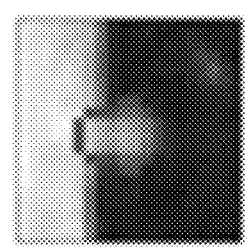
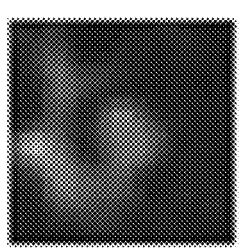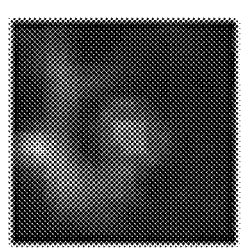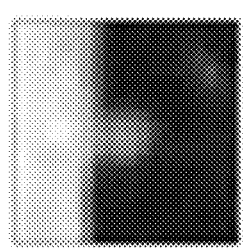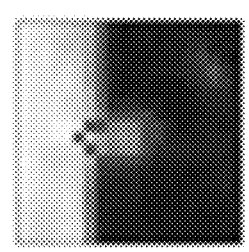
FIG. 2A   FIG. 2B   FIG. 2C   FIG. 2D

FIG. 3A

| P476137 | | 11/10/15 | 2/4/16 | 4/5/16 | 5/27/16 | 7/22/16 | 12/28/16 | 12/21/18 |
|---|---|---|---|---|---|---|---|---|
| Date | | | | | | | | |
| Days since 1st image | | 0 | 86 | 147 | 199 | 255 | 414 | 1137 |
| Days since previous image | | 0 | 86 | 61 | 52 | 56 | 159 | 723 |
| Number of lesions (N$_L$) | | 67 | 79 | 80 | 83 | 81 | 57 | 57 |
| Total lung lesion burden (V_sum) | | | | | | | | |
| Volume (mm$^3$) | | 12791 | 16338 | 20450 | 22043 | 21861 | 8053 | 7744 |
| Doubling Time (days) | | Base | 244 | 188 | 480 | -4677 | -110 | -12846 |
| ΔV_sum% (Base) | | | 28% | 60% | 72% | 71% | -37% | -39% |
| ΔV_sum% (previous) | | | 28% | 25% | 8% | -1% | -63% | -4% |
| Distribution of lesion volume | | | | | | | | |
| V_max (mm$^3$) | | 1464 | 1910 | 2007 | 2074 | 2104 | 935 | 755 |
| V_mean (mm$^3$) | | 191 | 207 | 256 | 266 | 270 | 141 | 136 |
| V_SD (mm$^3$) | | 283 | 326 | 387 | 388 | 399 | 199 | 185 |
| R$_L$ | | 0.162 | 0.167 | 0.158 | 0.148 | 0.151 | 0.170 | 0.165 |
| 3D distribution of lesions on a NORMALIZED lung volume | | | | | | | | |
| Dimensions of 3D map | D$_x$ | 0.847 | 0.851 | 0.855 | 0.855 | 0.856 | 0.838 | 0.784 |
| | D$_y$ | 0.634 | 0.669 | 0.651 | 0.611 | 0.683 | 0.657 | 0.624 |
| | D$_z$ | 0.653 | 0.673 | 0.645 | 0.723 | 0.657 | 0.657 | 0.636 |
| Centroid of 3D map | X$_c$ | 0.500 | 0.497 | 0.486 | 0.484 | 0.467 | 0.477 | 0.510 |
| | Y$_c$ | 0.450 | 0.444 | 0.427 | 0.443 | 0.456 | 0.444 | 0.425 |
| | Z$_c$ | 0.589 | 0.605 | 0.595 | 0.604 | 0.598 | 0.578 | 0.577 |
| SD of 3D distribution | X$_{SD}$ | 0.280 | 0.277 | 0.275 | 0.279 | 0.273 | 0.282 | 0.283 |
| | Y$_{SD}$ | 0.155 | 0.157 | 0.161 | 0.160 | 0.162 | 0.179 | 0.168 |
| | Z$_{SD}$ | 0.180 | 0.178 | 0.173 | 0.185 | 0.177 | 0.183 | 0.171 |
| Principal component value | 1st | 0.0831 | 0.0827 | 0.0797 | 0.0841 | 0.0808 | 0.0876 | 0.0853 |
| | 2nd | 0.0279 | 0.0258 | 0.0295 | 0.0295 | 0.0272 | 0.0343 | 0.0288 |
| | 3rd | 0.0239 | 0.0245 | 0.0223 | 0.0237 | 0.0242 | 0.0235 | 0.0232 |

FIG. 3B

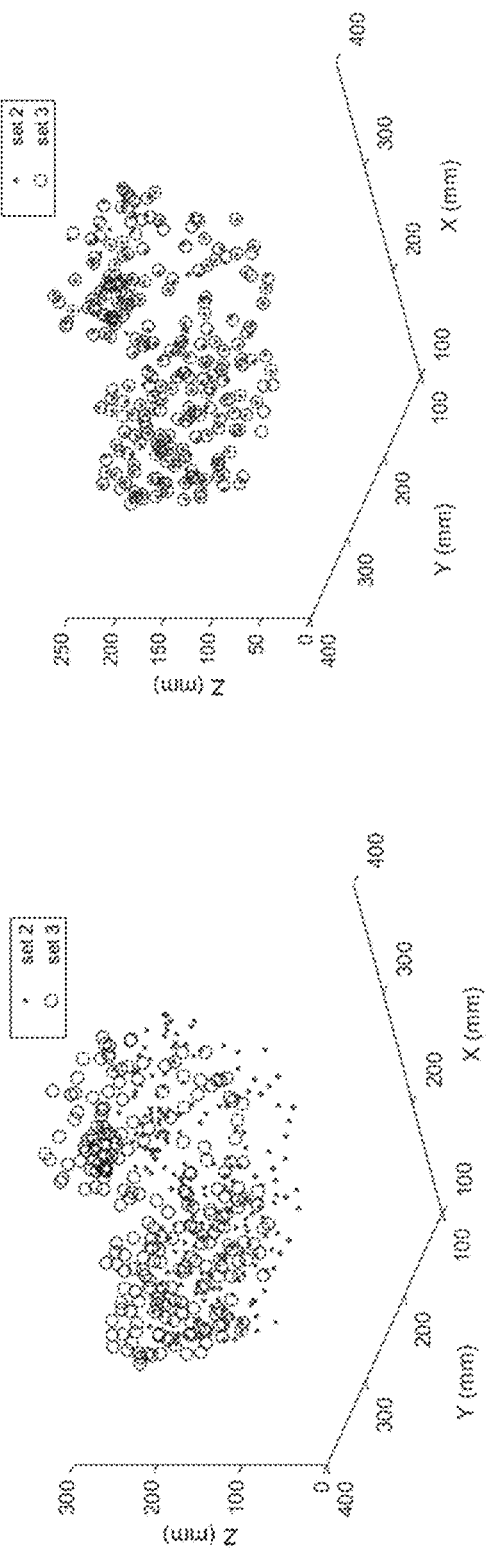
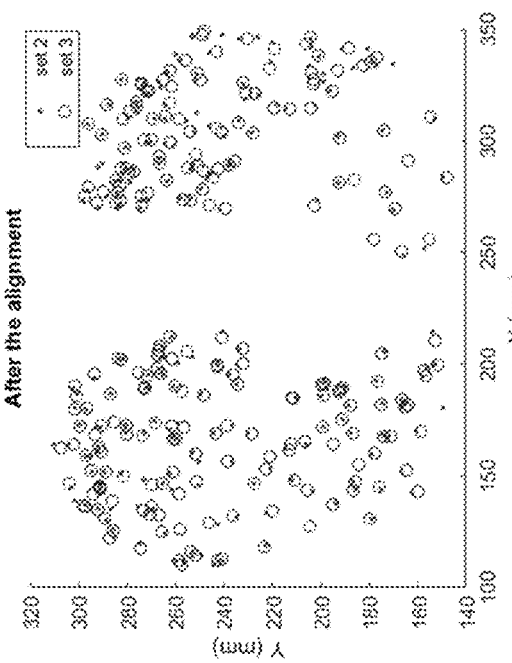
FIG. 4A
FIG. 4B
FIG. 4C

FIG. 7

| Images | Days | Lesion # | V_Max (mm³) | V_Sum (mm³) | RECIST 1.1 SLD (mm) | Radiologist report |
|---|---|---|---|---|---|---|
| Pt1_CT1 | 0 (+90d Rx1) | 138 | 175 | 4088 | 16 (8+8) | |
| Pt1_CT2 | 125 (+7d Rx2) | 153 | 222 | 5316 | 16 (8+8) | Progress (n=1) |
| Pt1_CT3 | 494 | 157 | 307 | 6721 | 17 (9+8) | Progress (n=6) |
| Pt1_CT4 | 729 | 257 | 695 | 15205 | 16 (18+8) | progress (n=5)/stable (n=1) |
| Pt2_CT1 | 0 | 4 | 85 | 203 | 9 (5+4) | |
| Pt2_CT2 | 73 | 7 | 120 | 541 | 9 (5+4) | stable* |
| Pt2_CT3 | 241 (+156d Rx1) | 17 | 157 | 779 | 10 (6+4) | progression (n=4)/stable |
| Pt2_CT4 | 472 | 30 | 196 | 1771 | 13 (7+6) | stable* |
| Pt2_CT5 | 646 | 36 | 379 | 3520 | 16 (8+8) | stable* |
| Pt2_CT6 | 665 | 41 | 443 | 4776 | 17 (9+8) | stable* |
| Pt2_CT7 | 875 (+160d_Rx 2/3) | 49 | 397 | 4288 | 16 (8+8) | stable |
| Pt2_CT8 | 1304 | 60 | 1479 | 13431 | 25 (14+11) | progression in lesion number and size (n=3) |
| Pt2_CT9 | 1449 | 63 | 1955 | 20280 | 30 (16+14) | stable* |
| Pt3_CT1 | 0 | 204 | 46243 | 88891 | 63 (44+19) | multiple lesions, (n=3) |
| Pt3_CT2 | 125 | 228 | 52339 | 112562 | 63 (44+19) | number of lesions >50, stable* (n=4) |
| Pt3_CT3 | 245 | 234 | 54983 | 137951 | 68 (48+20) | stable* (n=4) |
| Pt3_CT4* | 545 (+139d_Rx1) | 18 | 74454 | 85119 | 72 (50+22) | stable/regression/ progression (n=1) |
| Pt3_CT5 | 630 | 30 | 69313 | 78538 | 75 (52+23) | stable/regression |
| Pt3_CT6 | 728 | 30 | 71608 | 83178 | 75 (51+24) | regression (n=2)/ progression (n=1)/ stable (n=1) |
| Pt3_CT7 | 846 | 30 | 72175 | 84767 | 73 (50+23) | regression (n=1)/ progression (n=1)/ stable (n=2) |

FIG. 8

SYSTEM AND METHOD FOR QUANTITATIVE VOLUMETRIC ASSESSMENT AND MODELING OF TUMOR LESIONS

CROSS REFERENCE TO RELATED APPLICATION

This application claims priority to and benefit of U.S. provisional patent application Ser. No. 62/864,258 filed Jun. 20, 2019, which is fully incorporated by reference and made a part hereof.

GOVERNMENT SUPPORT CLAUSE

This invention was made with government support under grant numbers CA124570, CA168505 awarded by the National Institutes of Health. The government has certain rights in the invention.

BACKGROUND

Medical imaging is being used to render subjective visual assessment of tumor progression and/or treatment responsiveness. In order to be eligible to enroll in clinical trials, patients must have target lesion(s) measured in one diameter $\geq 10$ mm. Moreover, each enrolled patient will have no more than two lesions per organ being monitored per RECIST 1.1 recommendation. RECIST is a standard way to measure how well a cancer patient responds to treatment. It is based on whether tumors shrink, stay the same, or get bigger. To use RECIST, there must be at least one tumor that can be measured on x-rays, CT scans, or MRI scans. The types of response a patient can have are a complete response (CR), a partial response (PR), progressive disease (PD), and stable disease (SD). Also called Response Evaluation Criteria In Solid Tumors. This practice leads to at least two challenges: (1) For patients not being enrolled in clinical trials, their disease progression may not be properly monitored, leading to suboptimal clinical management; and (2) For patients being enrolled in clinical trials using RECIST 1.1 criteria to evaluate treatment response, assessment of their lesion progression and treatment responsiveness suffers from two limitations: a) quantitative assessment is based on two-dimensional (2D) measurement, and b) monitoring only a limited number of lesions neglects the effects of heterogeneous lesion dynamics.

Therefore, systems and methods are desired that overcome challenges in the art, some of which are described above. There is a need for a timely and accurate method to document the size (three-dimensional), location and evolving nature of tumor lesions in a target organ.

SUMMARY

Described herein are methods and mathematical models to render quantitative assessment, modeling, and prediction of lesion progression and/or treatment responsiveness. In one aspect, a system, method and computer program product are described that process digital images to locate, segment, and determine three-dimensional (3D) size of individual lesions in a target organ. When employed to analyze multiple successive images acquired before and after treatment, it is able to track changes in size of individual lesions to render quantitative assessment of lesion progression and/or treatment responsiveness. Moreover, it is able to use mathematical models to assess and predict continuous temporal progress and treatment responsiveness of individual lesions.

Embodiments disclosed herein provide several advantages including identification, 3D localization, and 3D segmentation of individual lesions in a target organ; automatic 3D size calculation of individual lesions; growth rate of lesions is automatically calculated using multiple ($\geq 2$) successive lesion sizes to establish quantitative and continuous temporal progress of individual lesions; treatment responsiveness of individual lesions can be quantitatively assessed and predicted using successive images prior to ($\geq 1$) and post ($\geq 2$) treatment; and a large number of individual lesions in a target organ may be identified and tracked. Therefore, heterogeneity in lesion dynamics can be examined and taken into consideration when conducting statistical analysis and planning clinical management.

The 3D spatial distribution of the identified lesions forms a unique 3D point structure. The 3D lesion distribution map captures the number of lesions, volume of each lesion, and spatial location of each lesion relative to pulmonary anatomic regions. Accordingly, the 3D map can serve as a 3D signature of the disease state for each patient. Multiple parameters extracted from the 3D signature are weighted by priority for the prognosis of patient disease development. The changes of these parameters during therapeutic intervention can provide important insight into the lesions' evolving trajectory and will be predictive of therapeutic responsiveness.

As noted herein, aspects of the disclosed embodiments can be realized as a software package serving as a clinical/research tool to assist radiologists and researchers to track and predict temporal progress and treatment responsiveness of individual lesions. It significantly reduces required time and efforts from radiologists or researchers. Software modules associated with different types of cancer are able to provide tailored clinically relevant information to empower physicians making evidence-based decision to select monitoring frequency, to initiate timely clinical intervention, and/or to switch in time alternative therapeutic regimen.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 1A is an original CT image, FIG. 1B is the segmented lung region, and FIG. 1C illustrates automatically identified and segmented lesions (lesions are shown numbered);

FIGS. 2A-2D illustrate examples of the automatic segmentation of juxtavascular/juxtapleural lesions with user defined initial seed point where FIG. 2A illustrates multiple slices of original CT image (along axial direction) for a juxtavascular lesion, and FIG. 2B illustrates corresponding image slices showing the segmented lesion; FIG. 2C illustrates multiple slices of original CT image (along axial direction) for a juxtapleural lesion, and FIG. 2D illustrates corresponding image slices showing the segmented lesion;

FIG. 3A illustrates an exemplary lesion data output file; FIG. 3B illustrates an exemplary temporal dynamics of parameters extracted from serial images in an individual patient;

FIG. 4A illustrates 3D spatial distribution of the lesions identified from two consecutive CT images before lesion co-registration;

FIG. 4B illustrates the 3D spatial distribution after applying lesion co-registration;

FIG. 4C illustrates a top view (two-dimensional) of the lesions identified from two consecutive CT images after applying lesion co-registration;

FIG. 7 is a tabular representation of information obtained by one of the disclosed embodiments FIG. 8 illustrates an exemplary lesion tracking summary obtained by at least one of the disclosed embodiments compared to a radiologist's report for three randomly selected patients;

DETAILED DESCRIPTION

Figure 1A:
FIGS. 1A, 1B, and 1C illustrate a process for automatic lesion identification and segmentation where

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems may be understood more readily by reference to the following detailed description of preferred embodiments and the Examples included therein and to the Figures and their previous and following description.

In the disclosed tumor lesion identification, segmentation, tracking and analysis system, a first step is determining location and size (three-dimensional) of tumor lesions in a target organ. Optionally, once initially located and measured, the temporal progress and treatment responsiveness of individual lesions can be determined by comparing volume change with preceding and/or subsequent images.

First, a target organ is selected. In the examples herein, this target organ may be a lung, but other organs are contemplated within the scope of embodiments described herein. Once a target organ is selected, the organ undergoes medical imaging. For example, the organ may undergo computerized tomography (CT) imaging, though other forms of medical imaging may be used. In one aspect, obtaining a three-dimensional image of at least a portion of the target organ comprises obtaining the three-dimensional image using a targeted imaging technique. Such targeted techniques can include using one or more of Positron Emission Tomography/Computed Tomography (PET/CT), Single Photon Emission Computed Tomography/Computed Tomography (SPECT/CT), Positron Emission Tomography Magnetic Resonance Imaging (PET MRI), fluorescence spectroscopy, and the like. In various embodiments, the targeted imaging techniques can comprise injecting the subject with a material and obtaining a three-dimensional image of at least a portion of the target organ using one or more cameras that detect the injected material. For example, the injected materials can comprise one or more of Technetium-99, F18, zirconium 89, iodine 123, iodine 124, iodine 125, copper 64, gallium 67, gallium 68, lutetium 177, xenon 133, indium 111, and the like. In other aspects, obtaining a three-dimensional image of at least a portion of the target organ comprises obtaining the three-dimensional image of at least a portion of the target organ using a non-targeted imaging technique. For example, the non-targeted imaging techniques can include using one or more of X-Ray, ultrasound, CT, MRI, and the like. It is to be appreciated that the term "target organ" may refer to any tissue, organ, growth or abnormality, bone section, and the like.

The captured images of the target organ undergo segmentation. For example, lung region segmentation. Once the images of the organ are segmented, for each segment of the target organ, lesions in that segment are identified and segmented. For example, lesion identification and segmentation in the lung region. A three-dimensional map is created of the lesions and their locations and a volumetric size of each lesion is determined. Lesion association between lesions identified from multiple successive images captured at different time periods allows additional analysis of the lesions, medical diagnostics, treatment efficacy, and the like.

Example Involving a Lung as a Target Organ

Lung Region Segmentation

The disclosed example is focused on, but not limited to, tumor lesions that are in the lung area. Therefore, the segmentation of the lung region from the 3D image (e.g., CT image) is a preprocessing step for the following lesion identification and segmentation. The segmented lung region is defined as the interested diseased area, and thus, the computation time for the lesion identification can be greatly reduced when comparing with searching for the lesions from the whole 3D CT images. In order to achieve accurate lung region segmentation results, several different categories of approaches have been developed by researchers, including, for example, thresholding-based method, boundary-based methods, shape model-based methods, edge-based methods, machine learning based methods, and the like.

In general, while all of these lung region segmentation methods may function well when there is no or little abnormality in the lung area, there is no any single segmentation method that can achieve globally optimal performance for all different abnormal cases. As described herein, the result of lung segmentation provides a confined 3D space to facilitate the following lesion identification and lesion tracking. The accuracy of the delineation of the lung boundary is not critical for the following lesion identification and segmentation. Therefore, the thresholding-based method, which is one of the most computation efficient and widely accepted lung segmentation approach, is implemented in this example to segment the lung region from the original 3D CT image.

The idea of using thresholding-based method for lung segmentation comes from the fact that the inside of the lung area is darker than other parts of the body that are around it in the CT images. Whereas the attenuation values in the CT images, measured in Hounsfield units, have specific ranges for different tissues, the actually values still may vary in different CT images due to many different factors, such as the imaging machine, the usage of contrast agent, and the kernel that is used to reconstruct the 3D CT images. Therefore, the key for thresholding-based method is to find the optimal threshold value for each individual CT image. As described herein, the adaptive thresholding is used for lung segmentation. The threshold is determined according to the histogram of the CT image by the following equation:

$$T_0 = (I_{bg} + I_{mb})/2 \qquad (1)$$

where $T_0$ is the adaptive threshold value, $I_{bg}$ is the peak attenuation value of the background and $I_{mb}$ is the peak attenuation value of the muscles and bones in the histogram.

Figure 1B:

FIG. 1A is an original CT image of a lung. According to the threshold $T_0$, the initial mask of the lung region can be extracted from the CT image. Then, a morphological flood fill operation is applied to the initial mask to fill the holes that are caused by the tumor lesions and the vessels. Thus, the final refined lung region is obtained. FIG. 1B presents an example of the segmented lung region by applying the above-mentioned lung region segmentation method to the original CT image, as shown in FIG. 1A.

Lesion Identification and Segmentation

After the completion of the lung segmentation, the region of interest for searching the locations of the lesions is determined. In the lesion tracking system, the next two steps are detecting the locations of the lesions, i.e., lesion identification, and quantitatively measuring the size of the lesions, which is realized by 3D lesion segmentation. In most cases, though not required, these two steps are performed together as the lesion segmentation is generally immediately implemented after the lesion is identified. Therefore, these two steps are described together in this section.

There are many different factors that would affect the appearance of the lesion in the CT image, such as the lesion's size, the lesion's shape, the lesion's location, and the like. The most common example of the lesion's size that influence the lesion identification is that some small lesions that have lower attenuation value may not be easily detected and separated from the background. A lesion's location is a factor that may prevent the lesions to be automatically identified, as some of the lesions are attached to the vessel (juxtavascular), or the pleural surface (juxtapleural). Many different approaches have been developed to improve the automatic lesion identification algorithms, such as gray level thresholding, template matching, morphological operators, clustering, and the like. However, these methods can only work in some specific scenarios and may not work well in other cases. Therefore, the disclosed software selects different image processing strategies for identifying and segmenting the lesions in different scenarios. In the disclosed lesion analysis system, the lesions are generally categorized into two groups: isolated lesions, and juxtavascular/juxtapleural lesions. All the isolated lesions can be automatically identified and segmented using the disclosed software, while those juxtavascular/juxtapleural lesions can be automatically segmented after a seed point or a confined region is appointed by a user for each specific juxtavascular/juxtapleural lesions.

Automatic Identification and Segmentation of Isolated Lesions

In general, the process of automatic lesion identification is performed in two steps: 1). Find the initial candidate lesions in the search region; 2). Remove the false positive lesions from the initial candidate lesions. Thresholding-base methods are the most commonly used in finding the initial candidate lesions. Whereas these approaches are capable of efficiently finding the lesions that have clear separation with the surrounding background, they have difficulties in detecting the juxtavascular lesions and juxtapleural lesions. Therefore, they are good fits for automatic identification of isolated lesion.

In one embodiment the disclosed embodiments, the multiple gray-level thresholding method is implemented to find the initial candidate lesions. In the segmented lung region, several different thresholds, from low to high, are applied to find the isolated regions. With the increase of the threshold, more and more new isolated regions can be detected. All the detected isolated regions would be defined as initial candidate lesions, which are then analyzed in terms of shape to differentiate between the lesions and the vessels. For each initial candidate lesion, its shape is evaluated by the 3D principle component analysis. According to the ratio of three eigenvalues obtained from the principle analysis of each lesion, the elongated vessels can be detected and removed from the initial candidate lesions. Thus, each of the remaining lesions is determined to be a real lesion, and its centroid position is regarded as the location of the corresponding lesion for the following lesion segmentation process.

Figure 1C:
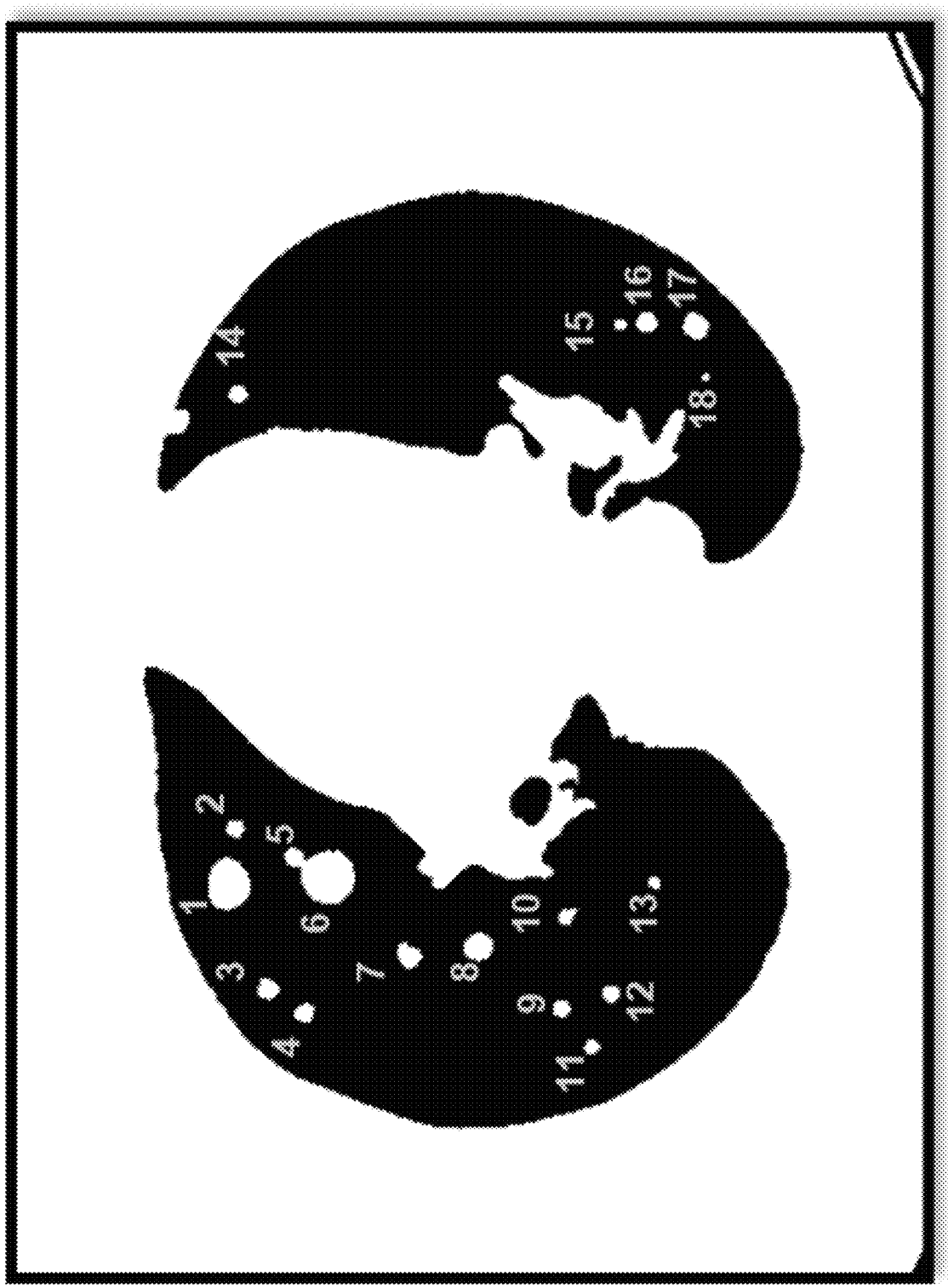

After the thresholding-based lesion identification method is implemented, the voxels above the threshold within each identified candidate lesion form a connected region, and provide the quantitative information of the lesion's size in 3D space. However, an arbitrary threshold cannot represent the boundary of the lesion for all different lesions and will result in inconsistency in the measured lesion volume across different lesions. In embodiments of the disclosed lesion analysis system, in order to make sure all the different kinds of lesions are measured under the same standard, the region-growing method is implemented for the segmentation of both isolated lesions and juxtavascular/juxtapleural lesions. The centroid position of each identified isolated lesions would be used as the seed point for the following region-growing based automatic lesion segmentation method. The detail of the region-growing method is discussed in section 2. As shown in FIG. 1C, all the isolated lesions in FIG. 1A can be correctly identified and segmented by using the automatic lesion identification and segmentation algorithm.

Automatic Lesion Segmentation with a User Defined Seed Point for Juxtavascular/Juxtapleural Lesions The 3D volumetric segmentation of juxtavascular/juxtapleural lesions is a challenging task as the 3D spatial relationship between the lesions and the vessels/pleural surface may vary for different lesions. There are many different lesion segmentation approaches that have been reported, including thresholding method, mathematical morphology method, region growing method, deformable model method, watersheds method, and the like. Whereas each of the above-mentioned method is capable of successfully segment the lesions from the vessels or the pleural surface in certain scenarios, none of these methods can be applied to various different situations and guarantee the segmentation results are correct. The reported successful rates of the lesion segmentation by using these methods vary from 83% to 91%.

In one of the disclosed embodiments, a region-growing based method is implemented to perform lesion segmentation for juxtavascular/juxtapleural lesions, as it is one of the proved methods that can provide accurate volumetric lesion segmentation results. The whole lesion segmentation process is automated after the initial seed point, which could be any voxel inside the target lesion, is appointed by the user. The implemented lesion segmentation algorithm can be described as the following four steps: 1) find the mask of the foreground; 2) calculation of the optimal seed point; 3) construct the priority map for region growing; and 4), peripheral-contrast based region growing on priority map.

1). Find the Mask of the Foreground

The first step of the region growing method is to find out the foreground (voxels with higher intensity) around the seed point. The foreground is used as the confined region that the region growing method is applied to. The detailed steps for finding the mask of foreground can be summarized as follows:
  a) Define a local 3D cubic volume with a predefined size of 40 mm in each dimension for optimal computation time, centered on the initial seed point, in the isotropic CT image as the volume of interest (VOI).
  b) Apply local adaptive segmentation by using local 3D mask to segment the foreground image content in the VOI.

c) Fill the holes of the segmented foreground image by using morphological hole filling algorithm.
d) If there are multiple segmented foreground regions, define the one that include the initial seed point as the foreground mask that represent the lesion.
e) Expand the foreground mask by using morphological operation of dilation to assure all the boundary of the lesion is included into the foreground mask $M_f$.

2). Calculation of the Optimal Seed Point

For consistent lesion segmentation results, a user-independent seed point need to be used to start the region growing. This is achieved by applying an iterative optimum seed point calculation approach. The calculation starts with the initial seed point that is pre-defined either by automatic lesion identification algorithm or by the user manually. At each iteration, a mask of the foreground $M_f$ is calculated. Then a central core of the mask $M_f$ is found by using a distance transform method to erode multiple layers of the mask $M_f$. And the voxels with the highest attenuation value in the central core is defined as the new seed point. This process is repeated until it converges to the same seed point, i.e., the optimum seed point.

3). Construct the Priority Map for Region Growing

After the optimum seed point is determined, the next step is to find the correct path for the growth of the region. In order to make sure that all the voxels with higher attenuation value and vicinity to the seed points are added to the growing region earlier than other voxels, a priority map that considering both the attenuation value and distance to the seed point is developed as:

$$W = W_I \times W_D, \tag{2}$$

where $$W_I = \frac{1}{1 + K_1/\hat{I}}$$

is characterized by the normalized attenuation value $\hat{I}$ of the voxel, and $$W_D = \frac{1}{1 + K_2 \cdot D}$$

is characterized by the distance D between the voxel and the optimum seed point. $K_1$ And $K_2$ are two weighting factors. The priority values of all the voxels in the mask $M_f$ are calculated to generate the priority map that would be used as reference for the following region growing.

4). Peripheral-Contrast Based Region Growing on Priority Map

In a region-growing based lesion segmentation method, when to stop the growth of the region, i.e., the halting criteria, is used as it directly affects the accuracy of the measured lesion's volume. A consistent halting criterion should be presented to get the region growing algorithm to stop at the desired boundary. In some embodiments disclosed herein, a peripheral-contrast-based region growing (PCBRG) method is implemented. Two terminologies, i.e., inner boundary and outer boundary, are introduced here to describe this PCBRG method. Internal boundary (IB) is defined as the boundary produced by the set of connected outermost voxels of the current region. The outer boundary (OB) is the set of voxels adjacent to the current region during the growing process. The peripheral contrast $C_p$ of a region is defined as the difference between the average attenuation value of the current OB, $\bar{I}_{OB}$, and the average attenuation value of the current IB, $\bar{I}_{IB}$, i.e.:

$$C_p = \bar{I}_{OB} - \bar{I}_{IB}, \tag{3}$$

The peripheral contrast reflects an average magnitude of the gradient of the pixels at the boundary of the evolving region.

Figure 3A:
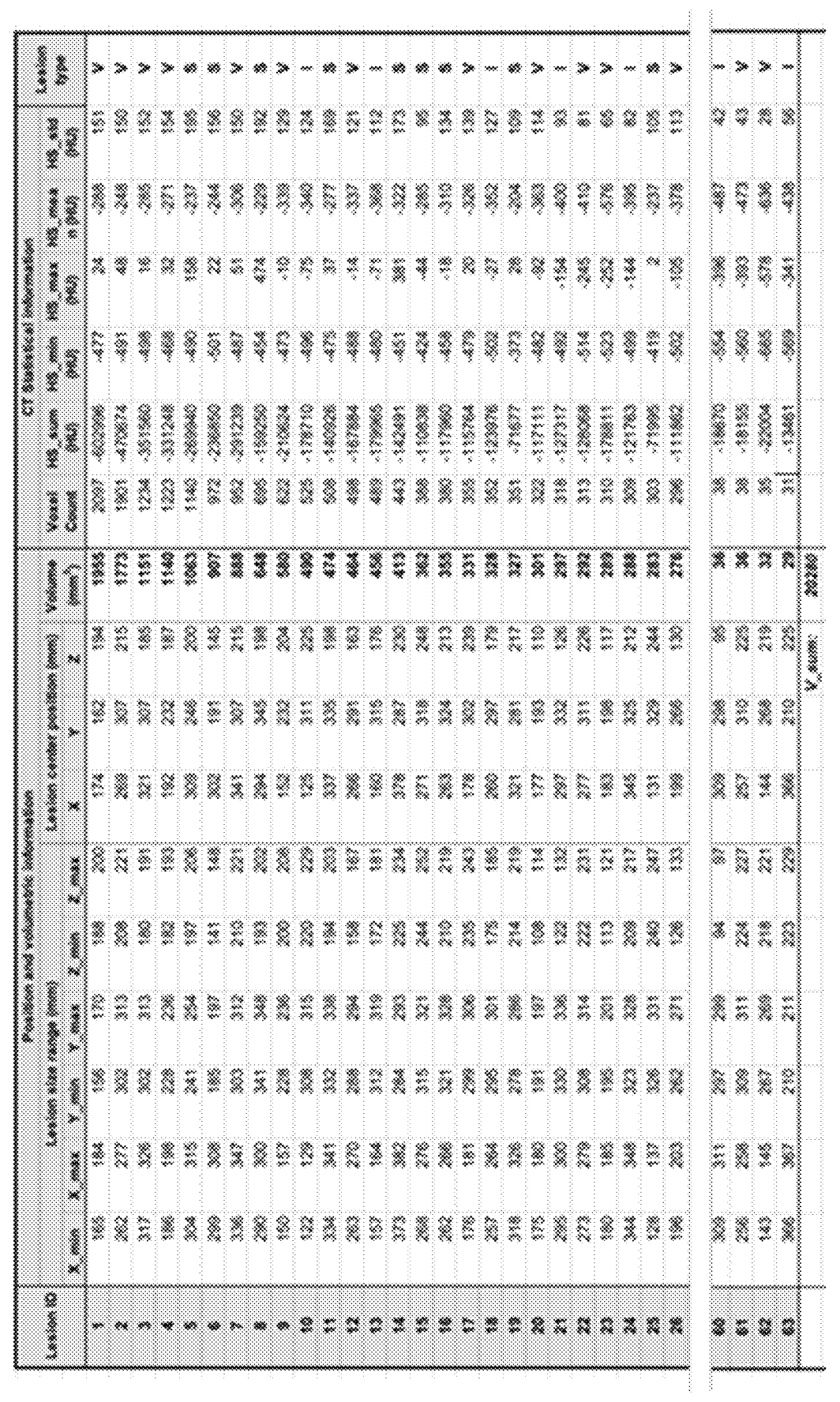

The region growing starts from the optimum seed point, and continues by adding the voxel with the highest priority value in the updated OB. After each new voxel is added into the growing region, the peripheral contrast $C_p$ is calculated. With the growth of the region, the $C_p$ reaches a local maximum, and it is used to define the segmented region. For most of the isolated lesions, the global maximum of $C_p$ can be used to determine the segmented region of the lesion. For the lesions that are interfered with vessels or pleural surface, multiple local maximums of $C_p$ can be recorded and different segmentation results can then be compared to determine the final segmentation results. FIGS. 2A-2D presents two examples of successfully segmented lesions in two different scenarios, i.e., one juxtavascular lesion and one juxtapleural lesion. FIG. 3A is a tabular display for lesion location (x,y,z coordinates), centroid position of each lesion, voxel-based calculation of lesion volume, CT number statistics, and lesion classification (I: isolated lesion, V: lesion attached to vessel, S: lesion attached to organ or pleural surface) indicative of individual lesion feature in a given CT image.

For each image of an individual patient, the 3D spatial distribution of the identified lesions forms a unique 3D point structure. The 3D lesion distribution map captures the number of lesions, volume of each lesion, and spatial location of each lesion relative to pulmonary anatomic regions. Accordingly, the 3D map can serve as a 3D signature of the disease state for each patient. Multiple parameters can be extracted from the 3D signature, including but not limiting to (a) the shape and dimension that define the outer boundary of the 3D lesion distribution map, which is defined by $D_X$, $D_Y$, $D_Z$ and Principal component values in FIG. 3B, (b) the centroid ($X_C$, $Y_C$, $Z_C$) and standard deviation ($X_{SD}$, $Y_{SD}$, $Z_{SD}$) of the lesion distributions within the normalized lung volume 3D working space, and (c) lesion density and local clustering of lesions. These quantitative measures are correlated with the disease states in individual patients before and after therapeutic intervention and among patients of different clinical outcome. Descriptions of parameters that quantify the 3D lesion distribution map are shown in Table I, below.

TABLE I

Parameters that Quantify 3D Lesion Distribution Map

| | |
|---|---|
| $N_T$ | The total number of lesions in each image. |
| $N_k$ | The number of lesions killed when compared to the previous image. |

TABLE I-continued

Parameters that Quantify 3D Lesion Distribution Map

| | |
|---|---|
| $N_n$ | The number of lesions newly emerged when compared to the previous image. |
| $N_i$ | The number of lesions "isolated" from adjacent vessels or organs. |
| $N_v$ | The number of lesions attached to vessels. |
| $N_s$ | The number of lesions attached to the lung/organ surface. |
| $(N_v + N_s)/N_i$ | The ratio between the number of attached lesion and isolated lesions. If this value increases, it may predict poor clinical outcome. |
| V_sum | The total lesion burden in each image. |
| V_max | The volume of the largest lesion in each image |
| $V_{mean}$ | The mean value of the lesion volumes from all lesions in each image. |
| $V_{SD}$ | The standard deviation of the lesion volumes from all lesions in each image. Larger $V_{SD}$ indicates greater variation in lesion volume. |
| $R_V$ | The complexity ratio Rv reflects the normalized variation of the lesion volumes regardless of lesion number. When the variation of the lesions volume increase, Rv will increase. |
| $S_i$ | Spherical shape index for each lesion. May indicate the likelihood of invasiveness (spreading) of the lesion. |
| $GR_{Vsum}$ | The growth rate of the V_sum from previous image to current image. |
| $GR_{Vmax}$ | The growth rate of the largest lesion from previous image to current image. |
| $GR_{mean}$ | The mean value of growth rates among all associated lesions in consecutive images. |
| $GR_{STD}$ | The standard deviation of growth rates among all associated lesions in consecutive images. |
| $(D_X, D_Y, D_Z)$ | The dimensions of the 3D lesion distribution map normalized along the x-axis of lung volume such that the distortion of the 3D map due to lung expansion during breathing is normalized between images. |
| $(X_C, Y_C, Z_C)$ | The centroid position of the normalized 3D lesion distribution map. This is an indicator of the average position of all lesions. |
| $(X_{SD}, Y_{SD}, Z_{SD})$ | The standard deviation of the normalized lesions' 3D positions along three different axes. It reflects the extent of variation of lesions' 3D positions in x, y, z axis within normalized lung region. |
| PCA | The three principle component values that reflect the shape and extent of the 3D distributed lesions. Similar to $(X_{SD}, Y_{SD}, Z_{SD})$, these values represent how widely the lesions spread in the 3D space. However, the PCA eigen values represent the lesions spread along three principle axes, independent of the normalized x, y, z axes, which may differ among image studies due to the addition of new lesions and/or disappearance of killed lesions. On the other hand, $(X_{SD}, Y_{SD}, Z_{SD})$ is defined according to a fixed normalized coordinate system. |
| Lesion density $(N_i/V_i)$ | Lesion density in a specific region. $N_i$ is the number of the lesion in the region, and $V_i$ is the volume of the corresponding lung region. It helps identify local clustering in each pulmonary lobes or segments. |

In addition, the degree of homogeneity for lesion spatial distribution within the 3D map is predictive of disease progression. The pattern of the lesion spatial distribution provides "the road map" of metastatic spread from primary cancer within the lung. Local clustering of lesions indicate regions permissive of metastasized cancer cells growth and expansion. For patients with consecutive CT-chest images, the growth rate (or tumor volume doubling time) for each lesion, which is enabled by lesion association (described herein), can be quantified and demonstrated as a 3D heatmap within corresponding pulmonary lobes/segments. It can also be determined if specific lung regions are uniquely permissive of rapid lesion growth and/or particularly responsive/resistant to various medical treatments. Changes in the pattern of 3D maps after medical intervention can be predictive/indicative of therapeutic responsiveness. Temporal dynamics of aforementioned quantitative parameters and/or 3D map patterns can be subjected to machine learning to evaluate interactions and the relative contribution of each parameter. This allows the identification of differently weighted variables that are most predictive of lesion progression and/or therapeutic responsiveness.

Lesion Association

After the completion of lesion identification and lesion segmentation for multiple sets of CT images that were taken at different dates; the location, volumetric size, and the statistical information of each identified lesion is recorded for each date. In order to track of change of each specific lesion from multiple CT images, the same lesion identified from different CT images is first associated. A pattern matching method is one of the most commonly used method to associate the same lesions identified from different CT images. The method compares the 3D CT image content inside and around the specific lesion between different CT images (taken at different dates) to find the correct lesion association results. However, there may be challenges to using 3D pattern matching in all instances.

In some embodiments disclosed herein, a point set registration method is used that automatically co-registers multiple lesions identified from different CT images simultaneously. In this disclosed method, each lesion is represented by a point in the 3D space according to its centroid position, regardless of its volume. As noted above, for each individual patient, the 3D spatial distribution of the identified lesions forms a unique 3D point structure. Although the relative position between the lesions may change in different CT images due to the change of body gestures or the body twist, the fundamental 3D spatial structure of the lesions remains the same. Considering the unavoidable body gesture change and small body twist, a non-rigid point set registration method is implemented to co-register the lesions identified from different CT images of the same patient. In the non-rigid point set registration algorithm, the coherent point drift algorithm is utilized to impose the motion coherence among the points, so that the fundamental 3D point structure can be maintained.

FIGS. 4A-4C show an example of using point set registration to co-register the lesions that are identified from two consecutive CT images that were taken 4 months apart. For each individual image set, more than 200 lesions were identified, 228 lesions for set 1 and 234 lesions for set 2. It has been verified that there are 216 associated lesion pairs between these two CT images. FIG. 4A shows the 3D distributions of the lesions identified from two CT images, and FIGS. 4B and 4C provide the 3D view and top view of the lesions after applying the lesion co-registration. Both views verified that most of the lesions are correctly co-registered. After reviewing each pair of the co-registered lesions, for the 216 associated lesion pairs, there are five pairs of the lesions that are not correctly associated, which is caused by the wrong co-registration to one of the adjacent lesions. In some of the disclosed embodiments, if the automatic lesion co-registration was not correct for a specific lesion pair, the software provides multiple candidates of the co-registered lesion to allow user to conveniently select the correct one.

The centroid locations of individual lesions in each CT image as shown in FIG. 3A are used to construct the images of FIGS. 4A-4C.

If there are more than two CT images for the same patient, the lesions identified from each two consecutive image sets need to be co-registered first. Then the lesions can be associated from the first CT image to the last CT image based on the previously obtained lesion co-registration information between each two consecutive CT images.

In some cases, the lesion may be missed and not identified from one set of CT image. This kind of situation can easily be discovered after the lesion association from first to the last CT images. According to the location of the same lesion in the CT image that it was identified, and the coordinate transform relationship that is calculated by using point set registration method between the CT images, the location of the lesion in the CT image in which the lesion was missed can be predicted by embodiments of the lesion analysis system disclosed herein. This allows the user to efficiently re-examine the CT image to find out the reason that the lesion was missed, and also provide the opportunity of adding the missed lesion back.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for tumor lesion identification, segmentation, tracking and analysis. In one exemplary aspect, the units can comprise a computing device that comprises a processor 421 as illustrated in FIG. 5 and described below.

Figure 5:
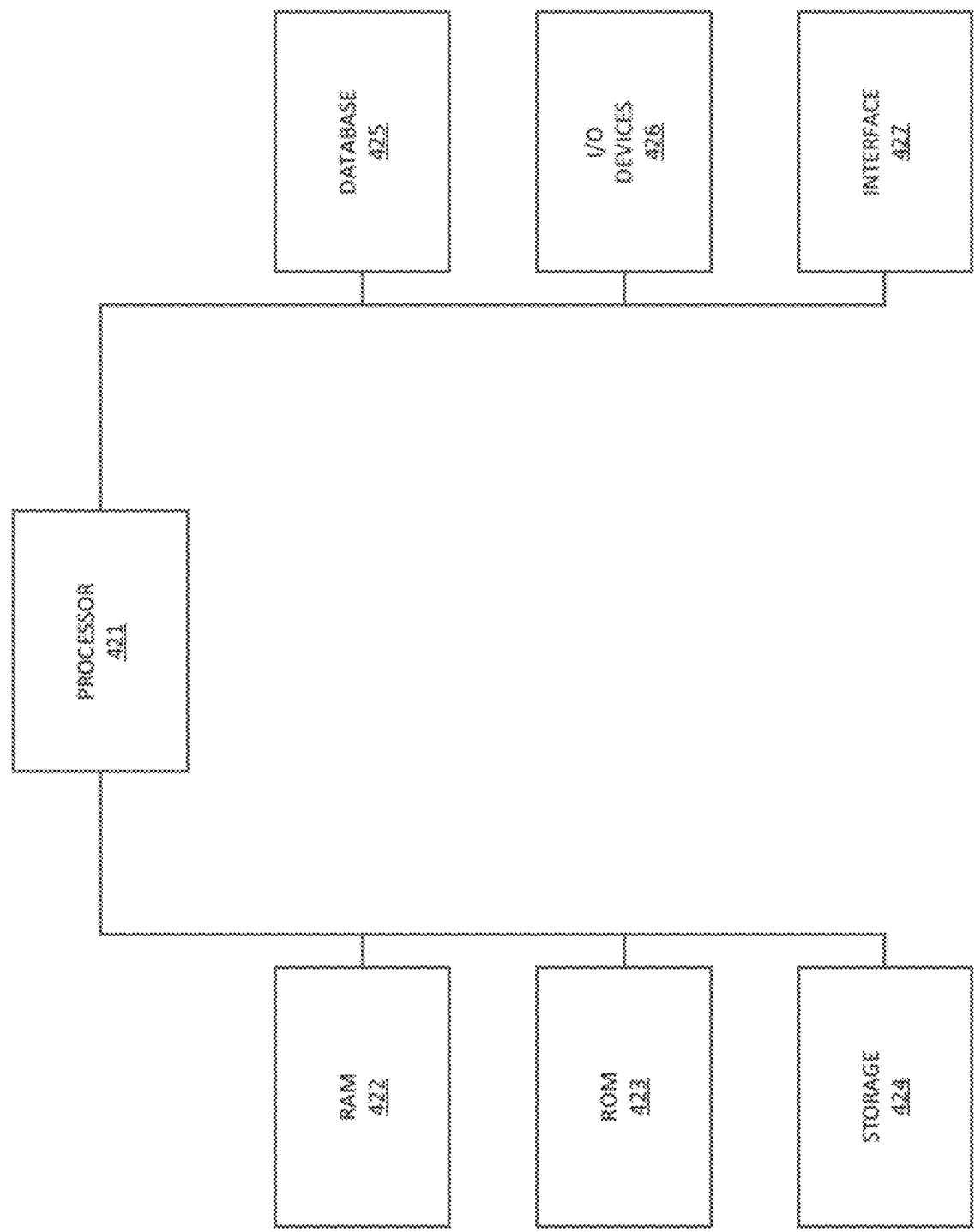
FIG. 5 illustrates an exemplary computer that can be used for tumor lesion identification, segmentation, tracking and analysis.

FIG. 5 illustrates an exemplary computer that can be used for a tumor lesion identification, segmentation, tracking and analysis system. As used herein, "computer" may include a plurality of computers. The computers may include one or more hardware components such as, for example, a processor 421, a random access memory (RAM) module 422, a read-only memory (ROM) module 423, a storage 424, a database 425, one or more input/output (I/O) devices 426, and an interface 427. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 424 may include a software partition associated with one or more other hardware components. It is understood that the components listed above are exemplary only and not intended to be limiting.

Processor 421 may include one or more processors, each configured to execute instructions and process data to perform one or more functions associated with a computer for discriminating tissue of a specimen. Processor 421 may be communicatively coupled to RAM 422, ROM 423, storage 424, database 425, I/O devices 426, and interface 427. Processor 421 may be configured to execute sequences of computer program instructions to perform various processes. The computer program instructions may be loaded into RAM 422 for execution by processor 421.

RAM 422 and ROM 423 may each include one or more devices for storing information associated with operation of processor 421. For example, ROM 423 may include a memory device configured to access and store information associated with the computer, including information for identifying, initializing, and monitoring the operation of one or more components and subsystems. RAM 422 may include a memory device for storing data associated with one or more operations of processor 421. For example, ROM 423 may load instructions into RAM 422 for execution by processor 421.

Storage 424 may include any type of mass storage device configured to store information that processor 421 may need to perform processes consistent with the disclosed embodiments. For example, storage 424 may include one or more magnetic and/or optical disk devices, such as hard drives, CD-ROMs, DVD-ROMs, or any other type of mass media device.

Database 425 may include one or more software and/or hardware components that cooperate to store, organize, sort, filter, and/or arrange data used by the computer and/or processor 421. For example, database 425 may store 3D digital images of a target organ, computer-executable instructions for tumor lesion identification, segmentation, tracking and analysis, and the like. It is contemplated that database 425 may store additional and/or different information than that listed above.

I/O devices 426 may include one or more components configured to communicate information with a user associated with computer. For example, I/O devices may include a console with an integrated keyboard and mouse to allow a user to maintain a database of digital images, results of the analysis of the digital images, metrics, and the like. I/O devices 426 may also include a display including a graphical user interface (GUI) for outputting information on a monitor. I/O devices 426 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 427 may include one or more components configured to transmit and receive data via a communication network, such as the Internet, a local area network, a workstation peer-to-peer network, a direct link network, a wireless network, or any other suitable communication platform. For example, interface 427 may include one or more modulators, demodulators, multiplexers, demultiplexers, network communication devices, wireless devices, antennas, modems, and any other type of device configured to enable data communication via a communication network.

Figure 6:
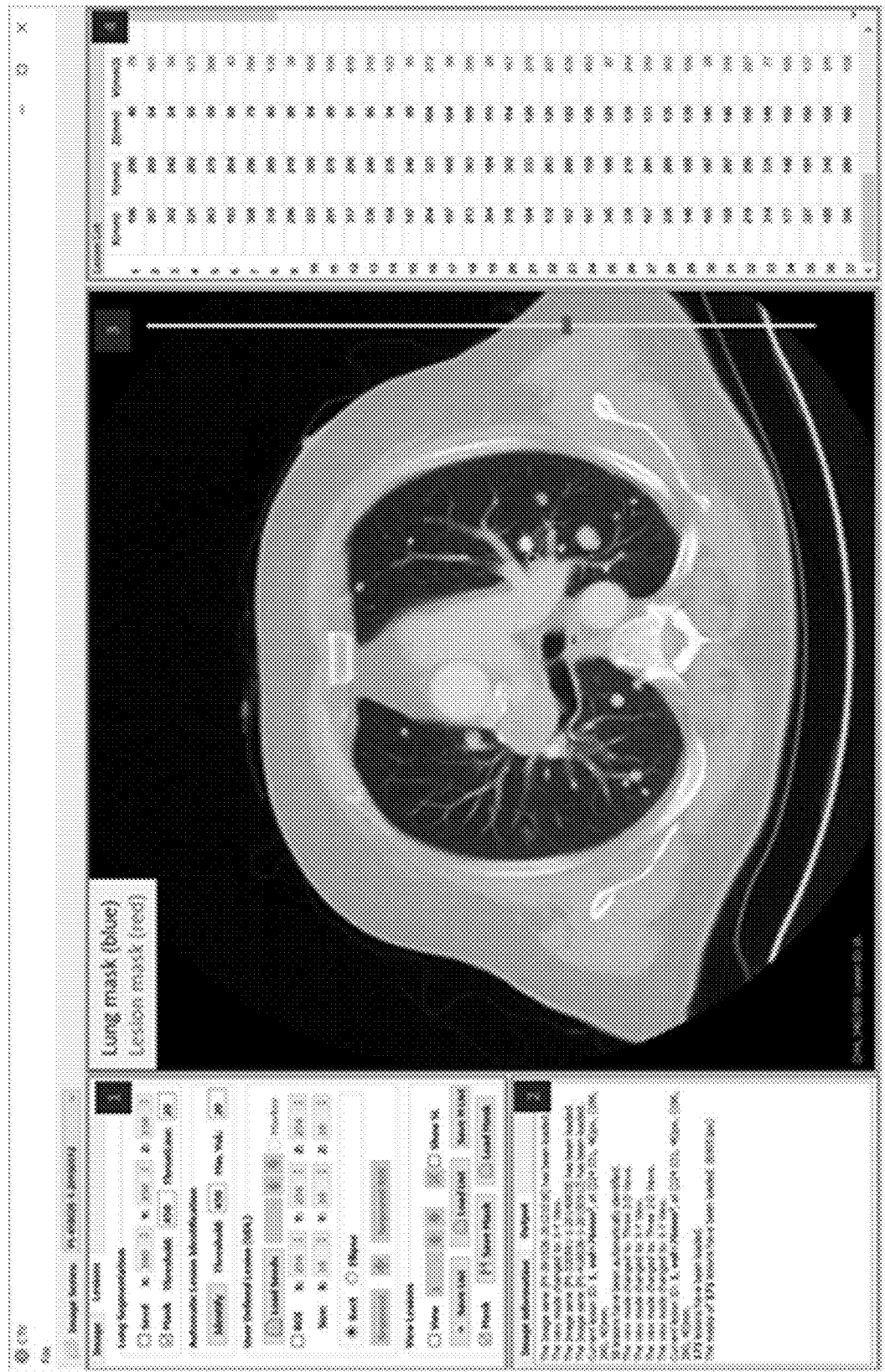
FIG. 6 shows the interactive platform display of exemplary CTViewer-lung software, which in this instance is comprised of four panels: 1). User control panel; 2). Information panel; 3). Image display panel; and 4). Lesion list panel.

An exemplary graphical user interface from one embodiment of the disclosed CTViewer-lung software used for CT-Chest image analysis is presented in FIG. 6. The shown interactive platform of the CTViewer-lung is composed of 4 panels:

1). User control panel: provides the user an interface to utilize different tools to run lesion analysis.
2). Information panel: There are two tabs in this panel, i.e., image information and output information. The image information tab shows the details of the patient and image related information obtained from the DICOM images. The output information tab records what tasks have been completed.
3). Image display panel: Displays the 3D image in 2D image slices from three orthogonal viewing angles (x, y, z). The results of lung and lesion segmentation can also be displayed immediately after lesion analysis.
4). Lesion list panel: Shows the list of the lesions that has been identified and segmented after lesion analysis, including the lesions' 3D positions, volumes, and 3-dimensional range.

Additional Examples and Uses

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in °C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

The disclosed embodiments are capable of conducting lung lesion identification, segmentation, and longitudinal tracking on changes in lesion volume. The workflow of applying on of the embodiments to analyze CT-chest images is described as follows: A DICOM file of CT-chest image is provided and loaded into a computing device having a display. The computing device displays on the display one or more (e.g., three) 2D views of the 3D image in three orthogonal directions. Automatic lung region segmentation starts immediately after a seed point inside the lung region is selected by the user, and identification and segmentation of "isolated" lung lesions are automatically conducted. In most instances, the aforementioned processes take less than 20 seconds to complete. All isolated lesions are marked in the image and their location and 3D volume is recorded by the computing system. The user then reviews the CT image slices and designates a seed point (any voxel within the lesion) for juxtavascular lesions or juxtapleural lesions. After a seed point is appointed, each of these lesions can be automatically segmented. In most instances this may occur within one second. Together with isolated lesions identified earlier, the location, 3D volumetric size, and the statistical information of the Hounsfield units, i.e. CT numbers, inside each segmented lesion, is all recorded and archived in a data file by the computing system. As shown in FIG. 3A, there are 63 lesions identified with lesion volume sizes ranging from 29 mm$^3$ to 1955 mm$^3$, and the total tumor burden is 20280 mm$^3$. The CT number statistics that include maximum, mean, standard deviation, and coefficient variance for each lesion are also provided as this information may serve as unique characteristics for each lesion. When multiple image studies have been analyzed, the parameters extracted from different image studies can be compared to show their temporal dynamics (FIG. 3B). The lesion volume related parameters, such as V_sum (total lung lesion burden), $$\Delta V\_sum \% \text{ (Base)} = \frac{V\_sum(i) - V\_sum(base)}{V\_sum(base)} \times 100\%,$$

$$\Delta V\_sum \% \text{ (previous)} = \frac{V\_sum(i) - V\_sum(i-1)}{V\_sum(i-1)} \times 100\%,$$

V_max (volume of the largest lesion), $V_{mean} +/- V_{SD}$ (mean and standard deviation of lesion volumes), and the 3D lesion distribution related parameters, such as $(X_C, Y_C, Z_C)$, $(X_{SD}, Y_{SD}, Z_{SD})$, and principle component values are extracted from different image studies and put together in sequence to monitor disease progression.

Figure 7:
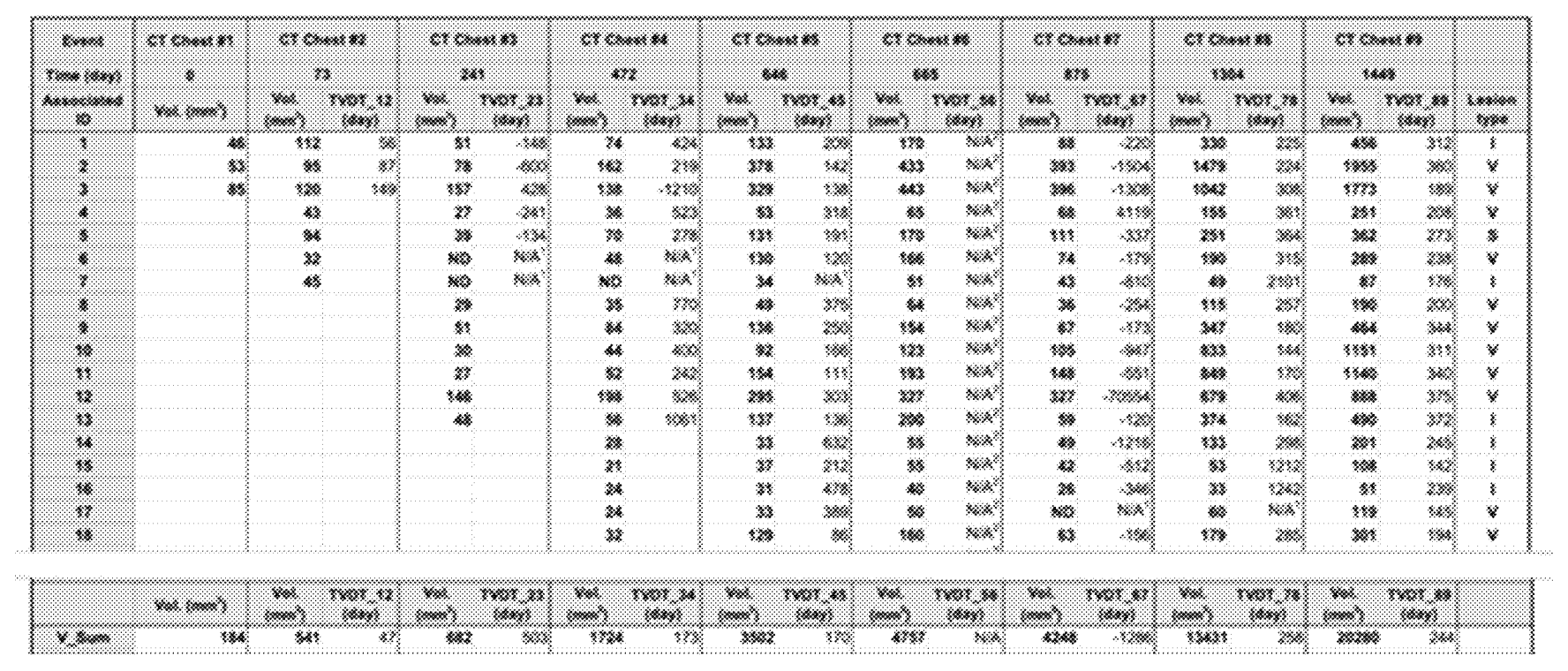

When there are serial CT-chest images available (taken at different times for the same patient), the lesions identified from each two consecutive images can be co-registered. In some instances co-registration may occur within about 20 seconds, or less. Consequently, lesion association among the serial CT-chest images can be accomplished to monitor longitudinal volume changes for each lesion. As shown in FIG. 7, the exemplary patient had three lung lesions detected at his/her first CT-chest image, with new lesions developed in time, he/she had 63 lung lesions at his last CT-chest image taken 1449 days after his first CT-chest image. The total lung lesion burden increased from 184 mm$^3$ to 20280 mm$^3$, more than a 100-fold increase in total lesion volume. The change in lesion volume for each lesion or for total lesion burden can be tracked longitudinally, which reflects lesion progression or regression in response to medical intervention. The speed of lesion progression can be monitored by calculating the days needed to double the lesion volume, i.e. doubling time, for each paired lesion.

In one example, lung lesion tracking and analysis was retrospectively conducted on serial CT-chest images from three patients and their lesions' progression and responsiveness to medical treatment were evaluated. FIG. 8 illustrates an exemplary lesion tracking summary obtained by at least one of the disclosed embodiments compared to a radiologist's report for three randomly selected patients where "Pt#" is the patient number (Pt1, Pt2, or Pt3); V_Max is the volume of the largest lesion; V_Sum is the volume summation of all the lesions; RECIST is response evaluation criteria in solid tumors; SLD is the sum of the longest diameters; Days are the number of days after Rx (medical treatment); n is the number of lesions with diameter measured by a radiologist; stable is the call by the radiologist as stable disease when it was actually progressing as indicated by an increase in the number of lesions and/or by an increase in V_Sum. As shown in FIG. 8, the patient 1 (Pt1) had four CT-chest images, the patient 2 (Pt2) had nine CT-chest images, and the patient 3 (Pt3) had seven CT-chest images analyzed. The time interval among CT-chest images are shown in days after the first CT-chest image. Embodiments disclosed herein provide the number of lung lesions identified, the volume of the largest lesion (V_Max), the summation of volume from all lesions identified (V_Sum).

The sum of the longest diameter (SLD) from the two largest lesions for each

CT-chest image per RECIST1.1, which has been used in clinical trials to assess patient's response to treatment can be readily extracted by the embodiments disclosed herein. As shown in FIG. 8 RECIST 1.1 SLD and the summary of radiologist report for each CT-chest image are compared with quantitative parameters extracted by CT-Viewer-lung. Note that both patients 1 and 2 would not be qualified to enroll in clinical trials due to the lack of measurable lesion with ≥10 mm in diameter until the very end stage, despite that their disease are progressing as indicated by the increase of lesion numbers and the increase in 3D volume of the largest lesion and total lesions burden. For patient 3, the unidimensional assessment of lesion burden per RECIST1.1 failed to demonstrate the significant decrease in total lesion burden in response to radioiodine treatment. Finally, subjective assessment on lesion progression by radiologist for patients not participating in clinical trials may not recognize disease progression that warrant alternative medical intervention.

Figure 9A:
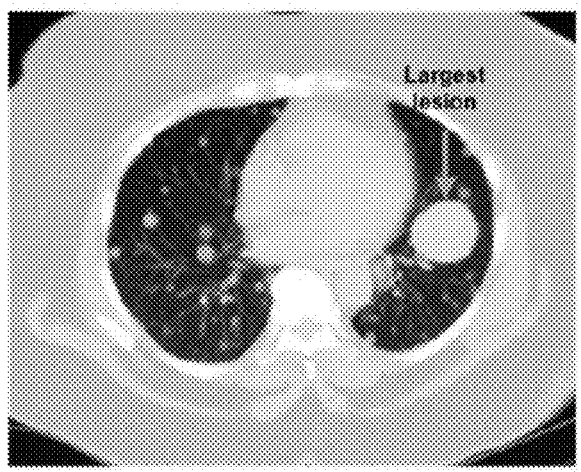
FIGS. 9A-9D show the trajectories of lesion growth in reference with the predicted exponential growth (e-growth) based on the dynamics of lesion volumetric measurement before radioiodine treatment for patient 3 identified in FIG. 8, above.
Figure 9B:
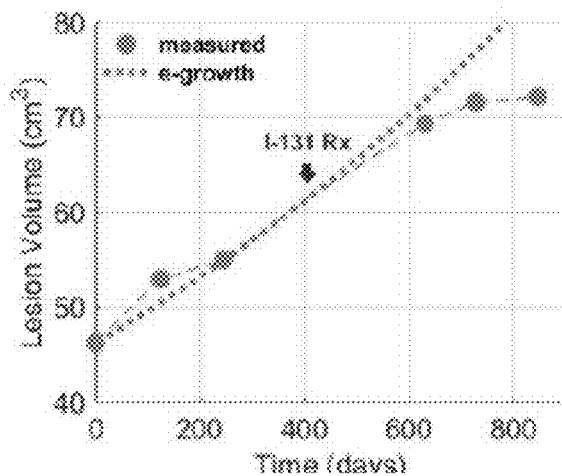
Figure 9C:
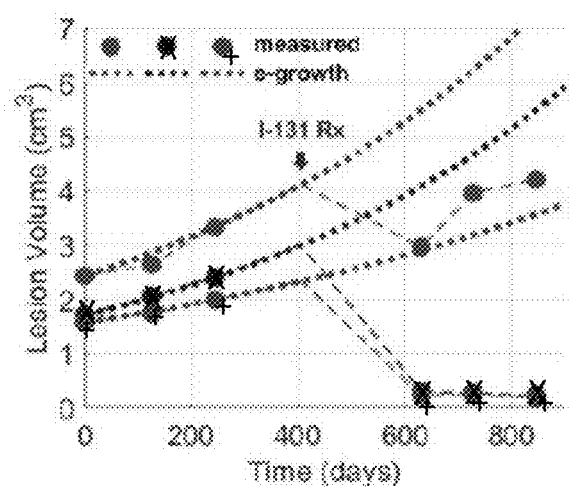
Figure 9D:
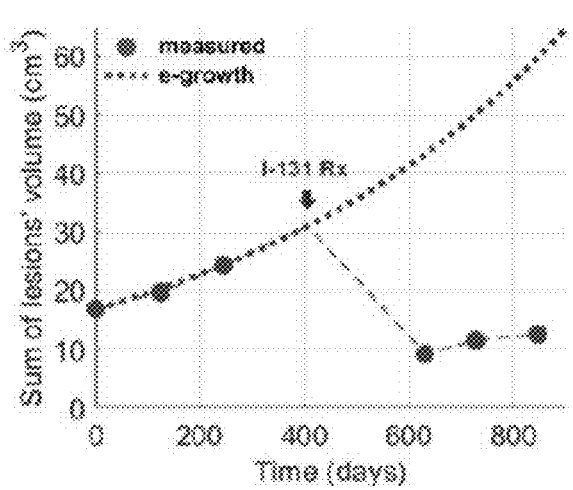

FIGS. 9A-9D show the trajectories of lesion growth in reference with the predicted exponential growth (e-growth) based on the dynamics of lesion volumetric measurement before radioiodine treatment for patient 3 where FIG. 9A shows a 2D CT image slice showing the largest lesion (lesion #1) in the lung region; FIG. 9B shows the progress of lesion #1 over time; FIG. 9C shows the progress of the next three largest lesions over time; and FIG. 9D shows the progress of the sum of all the lesions' volumes, except lesion #1, over time. FIG. 9A show the axial plane of CT-chest image with the largest lesion (~5cm in diameter), along with multiple lung lesions. The graph of FIG. 9B also show the growth trajectory of the largest lesion continues slowing down at 440 days after radioiodine treatment compared to the predicted e-growth curve plotted as the dotted line. The graph of FIG. 9C further show the volume of the second largest lesion was reduced significantly at 224 days post radioiodine treatment, and the survived tumor cells in this lesion seem to have accelerated growth rate at 322 days and then declined growth rate at 440 days post radioiodine treatment. The volume of the third and the fourth largest lesions reduced significantly at 224 days post radioiodine treatment and the volume of both lesions continue decreasing at 322 days and 440 days post-radioiodine treatment. Finally, the graph of FIG. 9D show the growth trajectory of the sum of all lesions excluded the largest lesion, indicating the sum of volume from 29 survived lesions are slightly increasing yet with declined growth rate.

Figure 10:
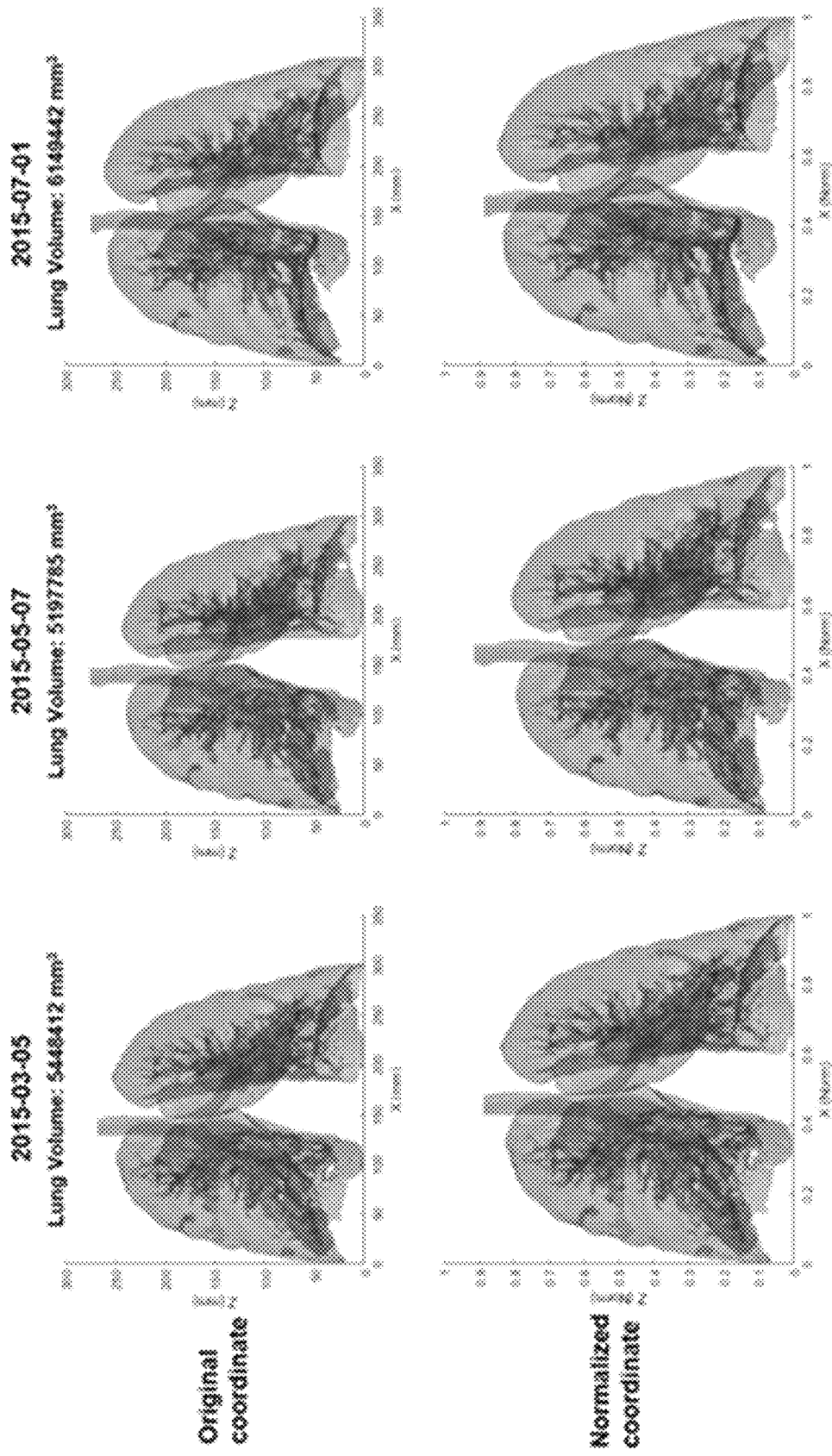
FIG. 10 are images that compare the original and normalized lung volumes among serial images from an exemplary patient. The images illustrate how the differences in lung volume caused by patient breathing at the time of image acquisitions are normalized.

FIG. 10 compares the change of both the original and normalized lung volumes among serial images from the same patient. The lung's volume varies among serial images of the same patient due to breathing differences at the time of image acquisition. After normalizing the coordinates based on the size of the lung in the x-axis, lung volume among serial images are comparable, and the segmented lungs can be aligned to compensate for differences in body gestures among serial image studies.

Figure 11:
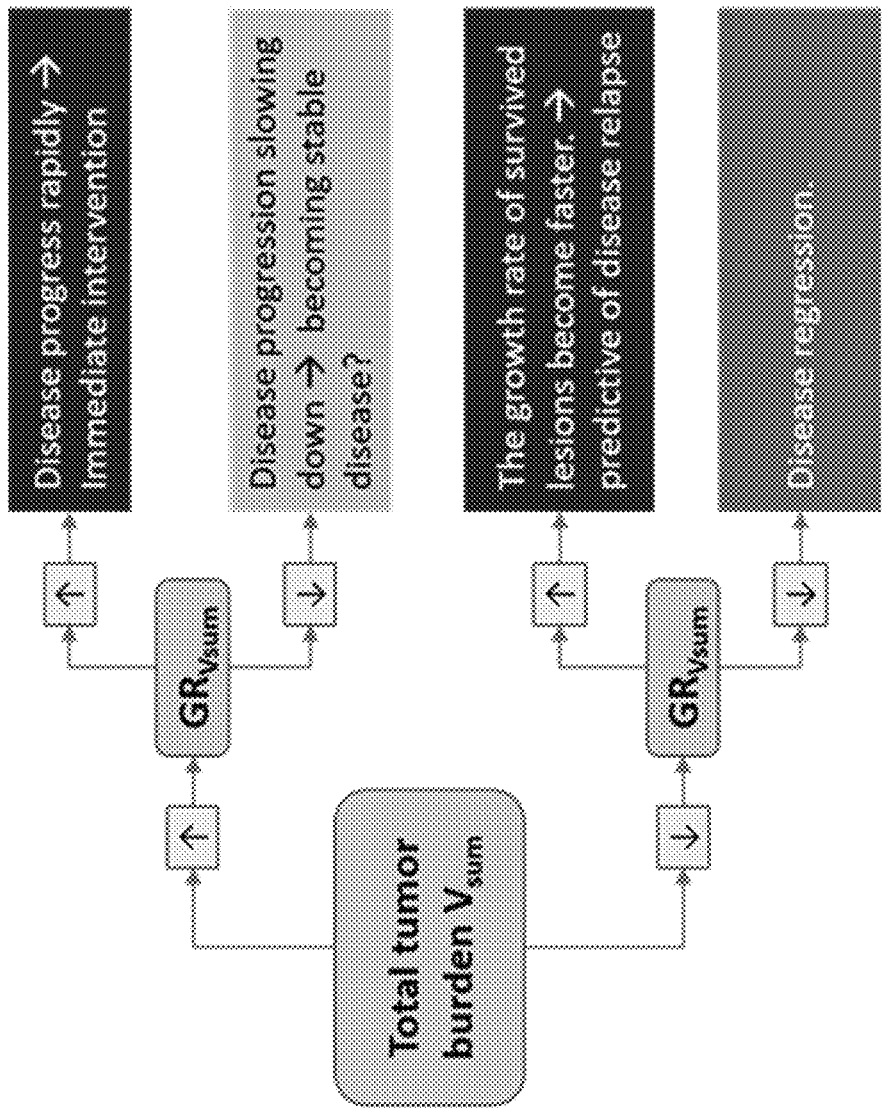
FIG. 11 is a decision chart showing clinical interpretations determined by joint changes in $V_{sum}$ and $GR_{Vsum}$. This demonstrates how the combinations of different changes in the two key parameters, i.e., $V_{sum}$ and $GR_{Vsum}$, affect clinical management.

FIG. 11 is a decision chart that demonstrates how the combinations of different changes in the two key parameters, i.e., $V_{sum}$ and $GR_{Vsum}$, affect clinical management. It shows that changes in $GR_{Vsum}$ plays a more effective role than $V_{sum}$ in guiding timely clinical management.

Figure 12A:
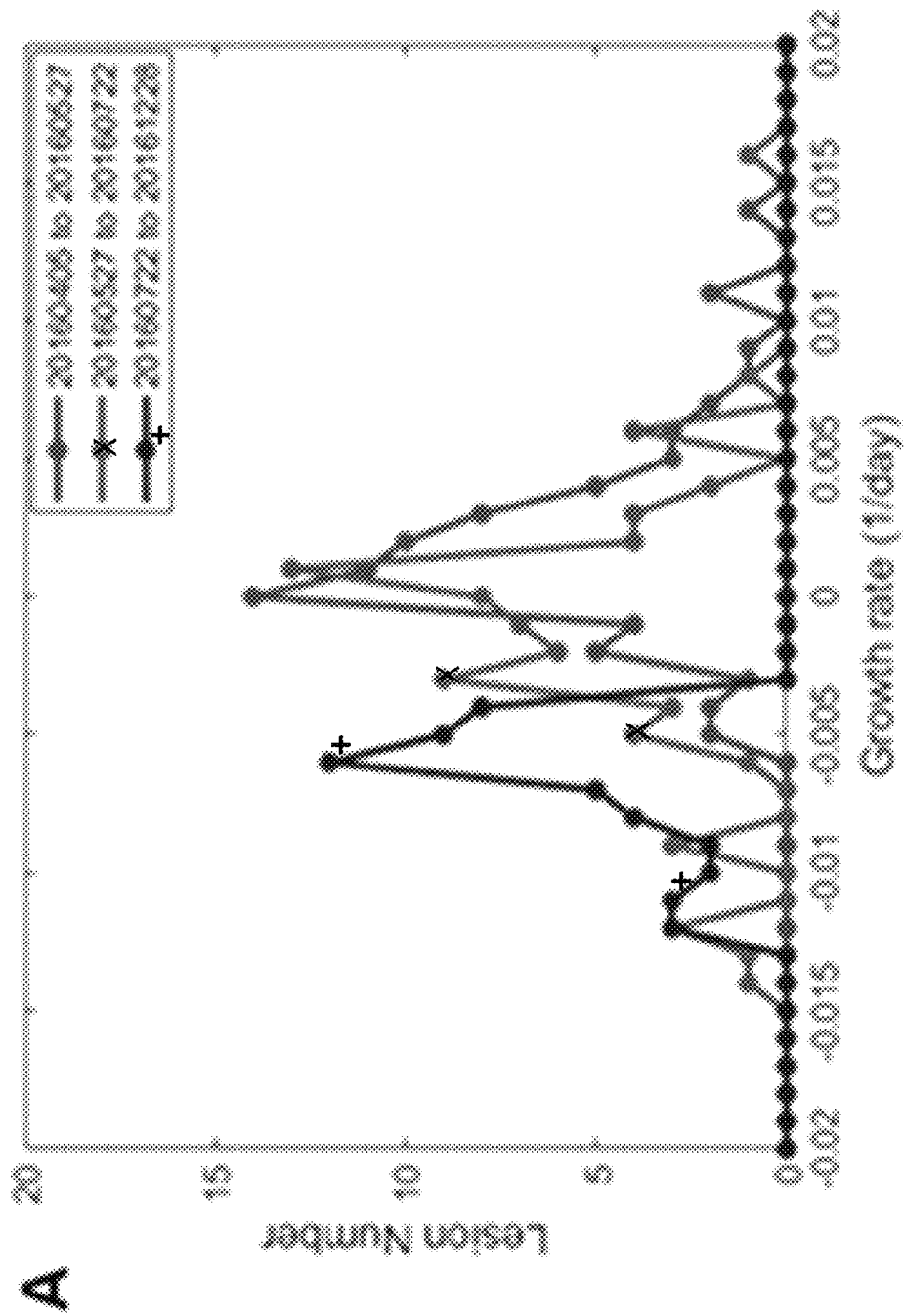
FIGS. 12A-12D present examples using the distributions of growth rates among associated lesions to predict subsequent clinical outcome.
Figure 12B:
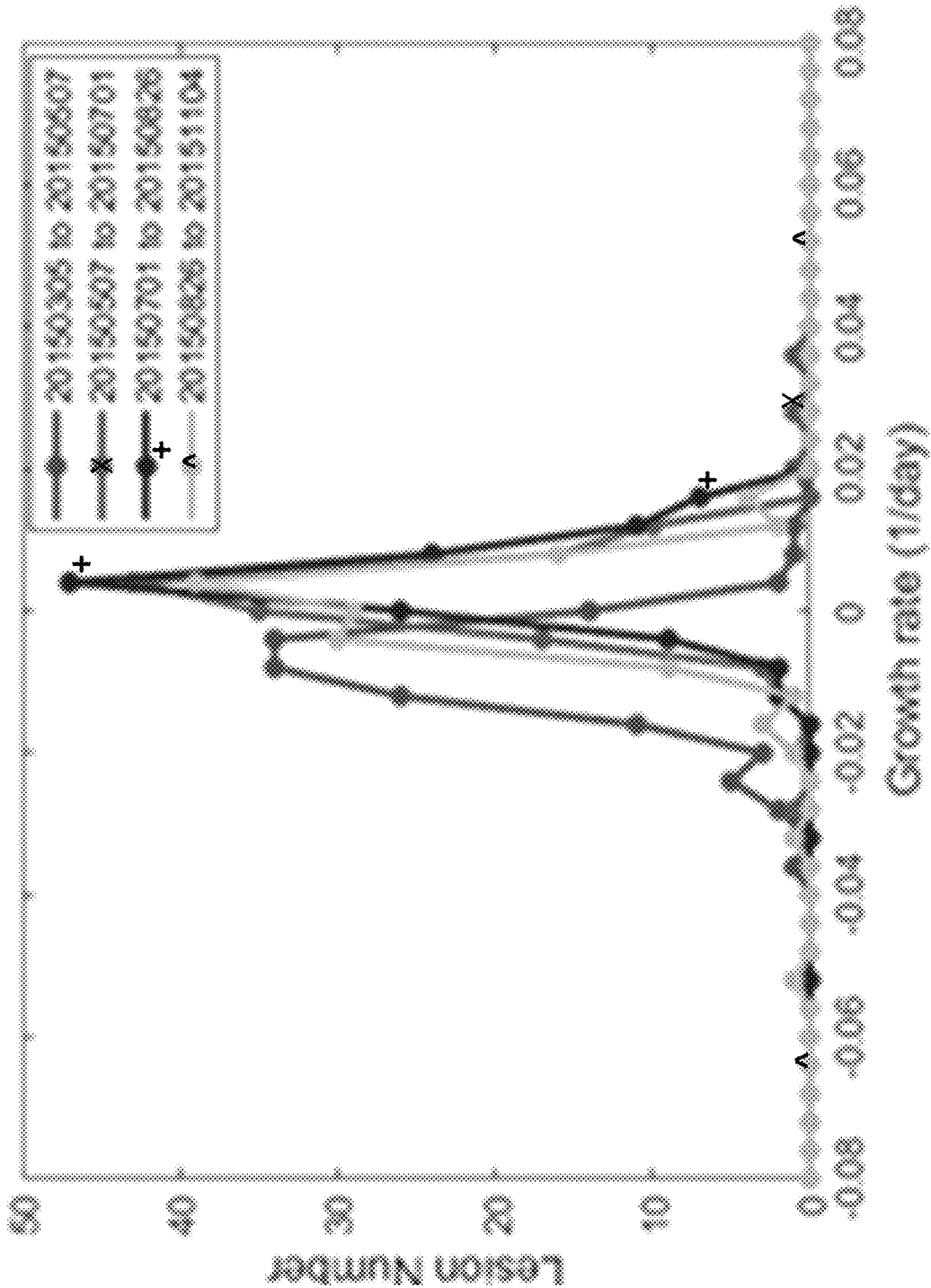
Figure 12C:
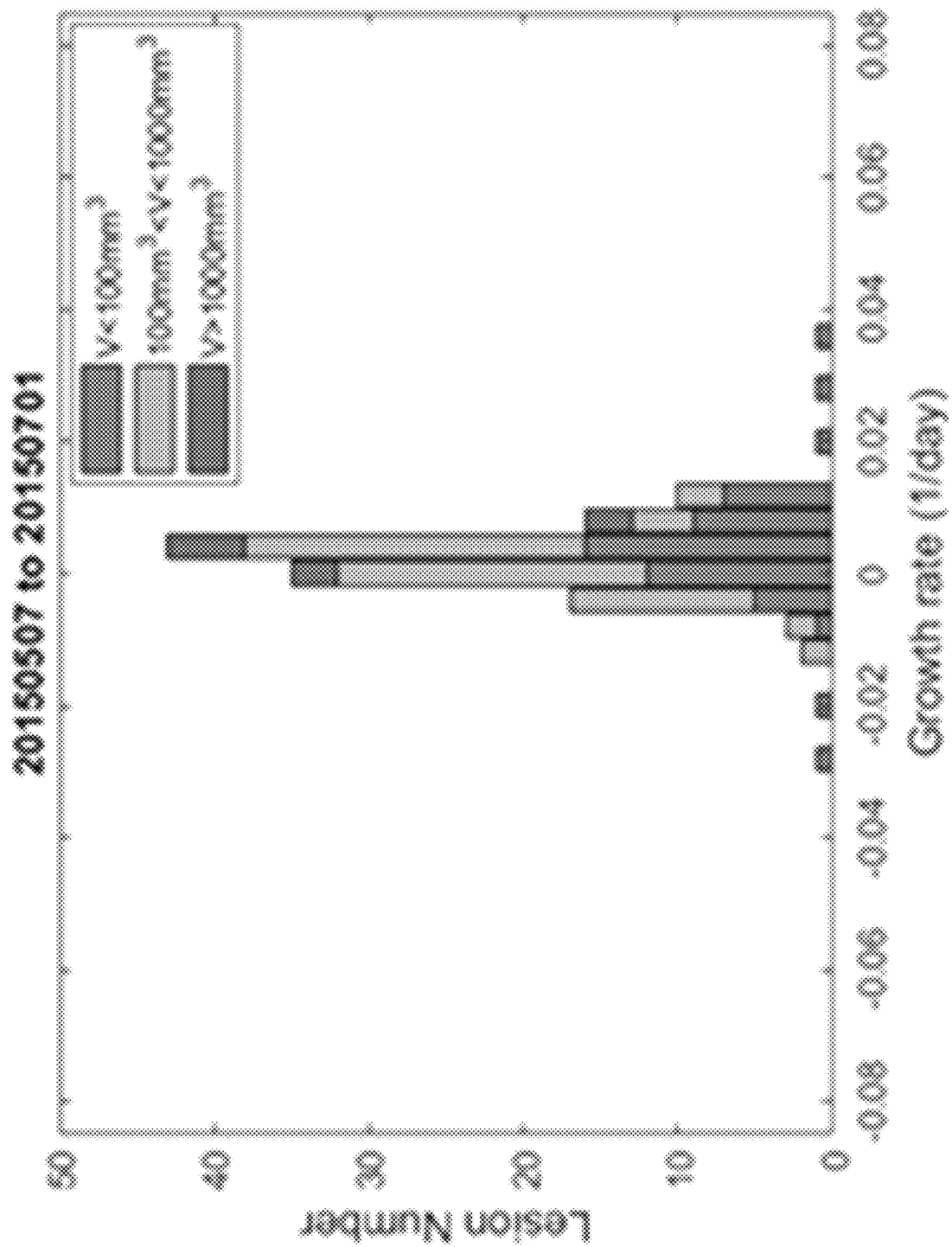
Figure 12D:
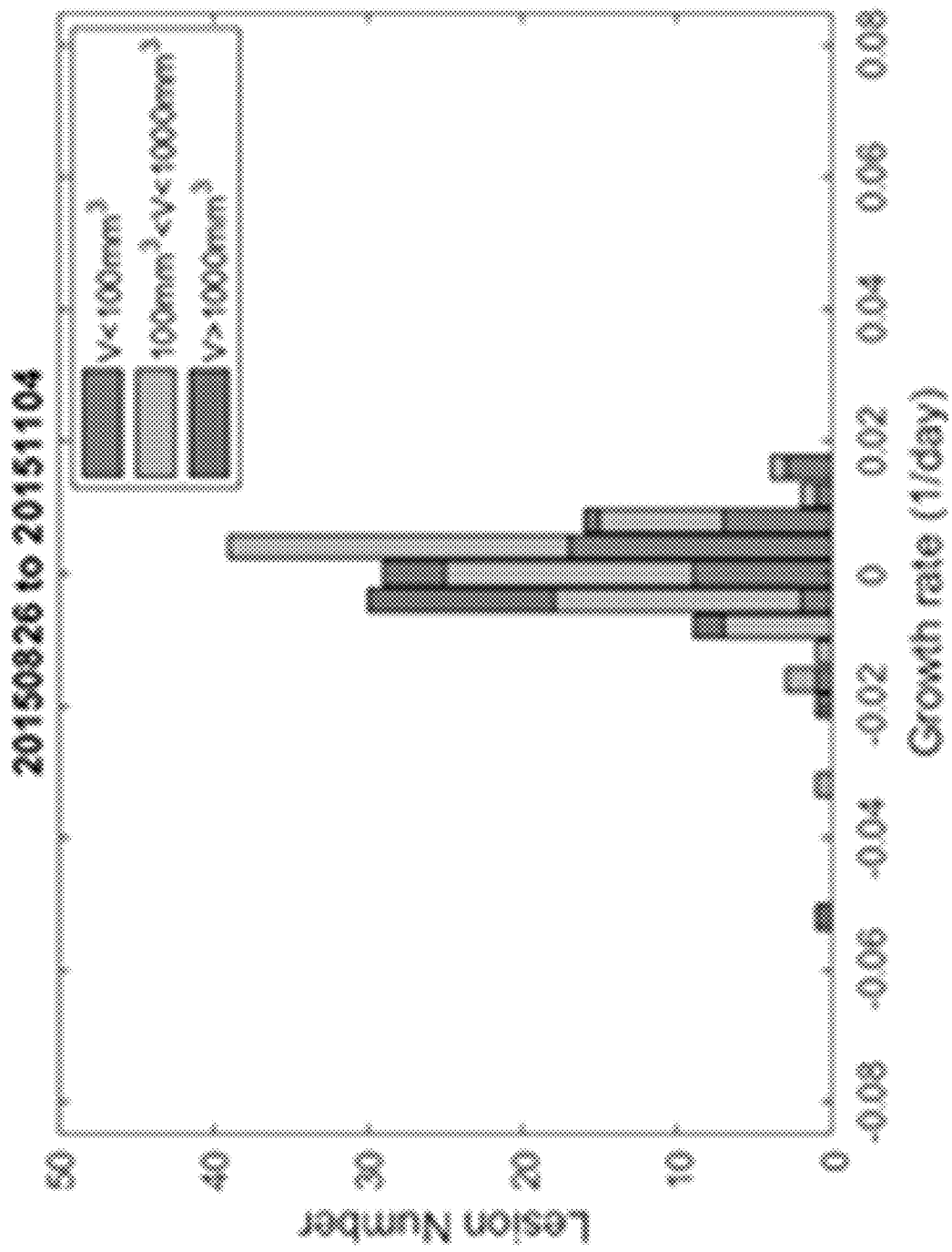

The distributions of growth rates (GR) among lesions in the same image study are characterized by two parameters: $GR_{mean}$ and $GR_{SD}$. In contrast to other parameters that can be directly extracted from each image study independently, these two parameters can only be obtained after lesion association from consecutive image studies. The GR distributions of associated lesions are plotted together to demonstrate the trend of lesion progression. If GR<0, lesion volumes are shrinking and vice versa. However, analyzing the changing rate of GR tends to better indicate long term prognosis. As shown in FIG. 12A, if the GR distribution of survived lesions shifts to the left in serial CT-chest images, that would indicate a good prognosis for the patient, since the lesions' growth rates are decreasing. FIG. 12B exemplifies when the GR distribution of survived lesions shifts to the right, which would indicate poor prognosis for this patient, as the lesions' growth rates are increasing. FIGS. 12C and 12D show the GR distribution among lesions of three categorized volume sizes, i.e. V<100 mm$^3$, 100 mm$^3$<V<1000 mm$^3$, and V>1000 mm$^3$. FIG. 12C is an example where the GR distribution is similar among lesions of the three categorized volume sizes. On the other hand, FIG. 12D is an example where the majority of the lesions with volume size >1000 mm$^3$ are shrinking (GR<0), while small and middle-sized lesions (<1000 mm$^3$) are continue growing (GR>0). Categorizing lesions by size and determining their specific GR distributions can reveal warning signs of future progression that may be overlooked otherwise.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain. These references, which are each incorporated by reference in their entireties, include but are not limited to:

1. G. J. Kemerink, R. J. Lamers, B. J. Pellis, H. H. Kruize, J. M. A. van Engelshoven, "On segmentation of lung parenchyma in quantitative computed tomography of the lung," *Medical Physics,* vol. 25, no. 12, pp. 2432-2439, 1998.
2. S. Hu, E. A. Hoffman, J. M. Reinhardt, "Automatic lung segmentation for accurate quantitation of volumetric X-ray CT images," *IEEE Transactions on Medical Imaging,* vol. 20, no. 6, pp. 490-498, 2001.

3. Y. Itai, H. Kim, S. Ishikawa et al., "Automatic segmentation of lung areas based on SNAKES and extraction of abnormal areas," in *Proceedings of the 17th IEEE International Conference on Tools with Artificial Intelligence (ICTAI '05)*, pp. 377-381, 2005.
4. M. Silveira, J. Nascimento, and J. Marques, "Automatic segmentation of the lungs using robust level sets," in *Proceedings of the 29th IEEE Annual International Conference of Medicine and Biology Society (EMBS '07)*, pp. 4414-4417, 2007.
5. I. Sluimer, M. Prokop, and B. Van Ginneken, "Toward automated segmentation of the pathological lung in CT," *IEEE Transactions on Medical Imaging*, vol. 24, no. 8, pp. 1025-1038, 2005.
6. M. Sofka, J. Wetzl, N. Birkbeck et al., "Multi-stage learning for robust lung segmentation in challenging CT volumes," in *Proceedings of the International Conference on Medical 27 Imaging Computing and Computer Assisted Intervention (MICCAI '11)*, pp. 667-674, 2011.
7. S. Sun, C. Bauer, and R. Beichel, "Automated 3D segmentation of lungs with lung cancer in CT data using a novel robust active shape model approach," *IEEE Transactions on Medical Imaging*, vol. 31, no. 2, pp. 449-460, 2012.
8. A. M. Mendonca, J. A. da Silva, and A. Campilho, "Automatic delimitation of lung fields on chest radiographs," in *Proceedings of the International Symposium on Biomedical Imaging (ISBI '04)*, vol. 2, pp. 1287-1290, 2004.
9. P. Campadelli, E. Casiraghi, and D. Artioli, "A fully automated method for lung nodule detection from postero-anterior chest radiographs," *IEEE Transactions on Medical Imaging*, vol. 25, no. 12, pp. 1588-1603, 2006.
10. P. Korfiatis, S. Skiadopoulos, P. Sakellaropoulos, C. Kalogeropoulou, and L. Costaridou, "Combining 2D wavelet edge highlighting and 3D thresholding for lung segmentation in thin-slice CT," *British Journal of Radiology*, vol. 80, no. 960, pp. 996-1005, 2007.
11. A. Mansoor, U. Bagci, Z. Xu, "A generic approach to pathological lung segmentation," *IEEE Transactions on Medical Imaging*, vol. 33, no. 12, pp. 2293-2310, 2014.
12. J. Yao, A. Dwyer, R. M. Summers, D. J. Mollura, "Computer-aided diagnosis of pulmonary infections using texture analysis and support vector machine classification," *Academic Radiology*, vol. 18, no. 3, pp. 306-314, 2011.
13. E. M. van Rikxoort, and B. van Ginneken, "Automated segmentation of pulmonary structures in thoracic computed tomography scans: a review," *Physics in Medicine & Biology*, vol. 58, no. 17, pp. R187-R220, 2013.
14. A. Mansoor, U. Bagci, B. Foster, Z. Xu, G. Z. Papadakis, L. R. Folio, F. K. Udupa, D. F. Mollura, "Segmentation and image analysis of abnormal lungs at CT: Current approaches, challenges, and future trends," *RadioGraphics*, vol. 35, no. 4, pp. 1056-1076, 2015.
15. S. G. Armato, M. L. Giger, C. J. Moran, J. T. Blackburn, K. Doi, and H. MacMahon, "Computerized detection of pulmonary nodules on CT scans," *Radiographics*, vol. 19, no. 5, pp. 1303-1311, 1999.
16. Q. Wei, Y. Hu, G. Gelfand and J. H. MacGregor, "Segmentation of lung lobes in high-resolution isotropic CT images," *IEEE Transactions on Biomedical Engineering*, vol. 56, no. 5, pp. 1383-1393, 2009.
17. A. El-Baz, G. M. Beache, G. Gimel'farb, K. Suzuki, K. Okada, A. Elnakib, A. Soliman, and B. Abdollahi, "Computer-Aided Diagnosis Systems for Lung Cancer: Challenges and Methodologies," *International Journal of Biomedical Imaging*, vol. 2013, 942353, 2013.
18. T. Matsumoto, H. Yoshimura, K. Doi et al., "Image feature analysis of false-positive diagnoses produced by automated detection of lung nodules," *Investigative Radiology*, vol. 27, no. 8, pp. 587-597, 1992.
19. A. A. Enquobahrie, A. P. Reeves, D. F. Yankelevitz, and C. I. Henschke, "Automated detection of pulmonary nodules from whole lung helical CT scans: performance comparison for isolated and attached nodules," in *Progress in Biomedical Optics and Imaging Medical Imaging: Imaging Processing, Proceedings of SPIE*, pp. 791-800, 2004.
20. Y. Lee, T. Hara, H. Fujita, S. Itoh, and T. Ishigaki, "Automated detection of pulmonary nodules in helical CT images based on an improved template-matching technique," *IEEE Transactions on Medical Imaging*, vol. 20, no. 7, pp. 595-604, 2001.
21. R. Wiemker, P. Rogalla, A. Zwartkruis, and T. Blaffert, "Computer aided lung nodule detection on high resolution CT data," in *Medical Imaging: Image Processing*, vol. 4684 of Proceedings of SPIE, pp. 677-688, 2002.
22. T. Ezoe, H. Takizawa, S. Yamamoto et al., "An automatic detection method of lung cancers including ground glass opacities from chest X-ray CT images," in *Medical Imaging: Image Processing*, vol. 4684 of Proceedings of SPIE, pp. 1672-1680, 2002.
23. K. Awai, K. Murao, A. Ozawa, M. Komi, H. Hayakawa, S. Hori, Y. Nishimura, "Pulmonary nodules at chest CT: effect of computer-aided diagnosis on radiologists' detection performance," *Radiology*, vol. 230, no. 2, pp. 347-352, 2004.
24. K. Kanazawa, Y. Kawata, N. Niki et al., "Computer-aided diagnosis for pulmonary nodules based on helical CT images," *Computerized Medical Imaging and Graphics*, vol. 22, no. 2, pp. 157-167, 1998.
25. M. N. Gurcan, B. Sahiner, N. Petrick, H. Chan, E. A. Kazerooni, P. Cascade, L. M. Hadjiiski, "Lung nodule detection on thoracic computed tomography images: preliminary evaluation of a computer-aided diagnosis system," *Medical Physics*, vol. 29, no. 11, pp. 2552-2558, 2002.
26. M. Tanino, H. Takizawa, S. Yamamoto, T. Matsumoto, Y. Tateno, and T. Iinuma, "A detection method of ground glass opacities in chest X-ray CT images using automatic clustering techniques," in *Medical Imaging: Image Processing*, vol. 5032 of Proceedings of SPIE, pp. 1728-1737, 2003.
27. J. P. Ko and M. Betke, "Chest CT: automated nodule detection and assessment of change over time—preliminary experience," *Radiology*, vol. 218, no. 1, pp. 267-273, 2001.
28. B. Zhao, M. S. Ginsberg, R. A. Lefkowitz, L. Jiang, C. Cooper, and L. H. Schwartz, "Application of the LDM algorithm to identify small lung nodules on low-dose MSCT scans," in *Proceedings of the Progress in Biomedical Optics and Imaging—Medical Imaging 2004: Imaging Processing*, pp. 818-823, 2004.
29. E. J. Candes, X. Li, Y. Ma, J. Wright, "Robust principal component analysis," *Journal of the ACM*, vol. 58, no. 3, pp. 1-37, 2011.

30. D. F. Yankelevitz, A. P. Reeves, W. J. Kostis, B. Zhao, and C. I. Henschke, "Small pulmonary nodules: volumetrically determined growth rates based on CT evaluation," *Radiology,* vol. 217, no. 1, pp. 251-256, 2000.
31. J. P. Ko, H. Rusinek, E. L. Jacobs et al., "Small pulmonary nodules: volume measurement at chest CT—phantom study," *Radiology,* vol. 228, no. 3, pp. 864-870, 2003.
32. W. Mullally, M. Betke, J. Wang, and J. P. Ko, "Segmentation of nodules on chest computed tomography for growth assessment," *Medical Physics,* vol. 31, no. 4, pp. 839-848, 2004.
33. W. J. Kostis, A. P. Reeves, D. F. Yankelevitz, and C. I. Henschke, "Three-dimensional segmentation and growth-rate estimation of small pulmonary nodules in helical CT images," *IEEE Transactions on Medical Imaging,* vol. 22, no. 10, pp. 1259-1274, 2003.
34. W. J. Kostis, D. F. Yankelevitz, A. P. Reeves, S. C. Fluture, and C. I. Henschke, "Small pulmonary nodules, reproducibility of three-dimensional volumetric measurement and estimation of time to follow-up CT," *Radiology,* vol. 231, no. 2, pp. 446-452, 2004.
35. J. M. Kuhnigk, V. Dicken, L. Bornemann et al., "Morphological segmentation and partial volume analysis for volumetry of solid pulmonary lesions in thoracic CT scans," *IEEE Transactions on Medical Imaging,* vol. 25, no. 4, pp. 417-434, 2006.
36. S. A. Hijjatoleslami, J. Kittler, "Region growing: A new approach", *IEEE Transactions on Image Processing,* vol. 7, pp. 1079-1084, 1998.
37. J. Dehmeshki, H. Amin, M. Valdivieso, and X. Ye, "Segmentation of pulmonary nodules in thoracic CT scans: a region growing approach," *IEEE Transactions on Medical Imaging,* vol. 27, no. 4, pp. 467-480, 2008.
38. S. Diciotti, G. Picozzi, M. Falchini, M. Mascalchi, N. Villari, and G. Valli, "3D segmentation algorithm of small lung nodules in spiral CT images," *IEEE Transactions on Information Technology in Biomedicine,* vol. 12, no. 1, pp. 7-19, 2008.
39. T. Kubota, A. K. Jerebko, M. Dewan, M. Salganicoff, and A. Krishnan, "Segmentation of pulmonary nodules of various densities with morphological approaches and convexity models," *Medical Image Analysis,* vol. 15, no. 1, pp. 133-154, 2011.
40. Y. Kawata, N. Niki, H. Ohmatsu, and N. Moriyama, "A deformable surface model based on boundary and region information for pulmonary nodule segmentation from 3D thoracic CT images," *IEICE Transactions on Information and Systems,* vol. 86, no. 9, pp. 1921-1930, 2003.
41. T. W. Way, L. M. Hadjiiski, B. Sahiner et al., "Computer-aided diagnosis of pulmonary nodules on CT scans: segmentation and classification using 3D active contours," *Medical Physics,* vol. 33, no. 7, pp. 2323-2337, 2006.
42. Y. Yoo, H. Shim, I. D. Yun, K. W. Lee, and S. U. Lee, "Segmentation of ground glass opacities by asymmetric multi-phase deformable model," in *Medical Imaging: Image Processing,* vol. 6144, February 2006.
43. L. R. Goodman, M. Gulsun, L. Washington, P. G. Nagy, and K. L. Piacsek, "Inherent variability of CT lung nodule measurements in vivo using semiautomated volumetric measurements," *American Journal of Roentgenology,* vol. 186, no. 4, pp. 989-994, 2006.
44. J. H. Moltz, M. Schwier, H. Peitgen, "A general framework for automatic detection of matching lesions in follow-up CT," 2009 *IEEE International Symposium on Biomedical Imaging: From Nano to Macro,* pp. 843-846, 2009.
45. A. Sotiras, C. Davatzikos, and N. Paragios, "Deformable Medical Image Registration: A Survey," *IEEE Trans Med Imaging,* vol. 32, no. 7, pp. 1153-1190, 2013.
46. A. Myronenko, X. Song, "Point set registration: coherent point drift," *IEEE Transactions on Pattern Analysis and Machine Intelligence,* vol. 12, pp. 2262-2275, 2010.
47. J. J. Erasmus, G. W. Gladish, L. Broemeling, B. S. Sabloff, M. T. Truong, R. S. Herbst, R. F. Munden, "Interobserver and Intraobserver Variability in Measurement of Non-Small-Cell Carcinoma Lung Lesions: Implications for Assessment of Tumor Response," *Journal of Clinical Oncology,* vol. 21, no. 13, pp. 2574-2582, 2003.
48. J. Egger, T. Kapur, A. Fedorov, S. Pieper, J. V. Miller, H. Veeraraghavan, B. Freisleben, A. J. Golby, C. Nimsky, R. Kikinis, "GBM Volumetry using the 3D Slicer Medical Image Computing Platform," *Scientific Reports,* vol. 3, pp. 1364, 2013.
49. B. Gaonkar, L. Macyszyn, M. Bilello, M. S. Sadaghiani, H. Akbari, M. A. Atthiah, Z. S. Ali, X. Da, Y. Zhan, D. O'Rourke, S. M. Grady, and C. Davatzikos, "Automated tumor volumetry using computer-aided image segmentation," *Academic Radiology,* vol. 22, no. 5, pp. 653-661, 2015.
50. W. Cai, and G. Hong, "Quantitative image analysis for evaluation of tumor response in clinical oncology," *Chronic diseases and translational medicine,* vol. 4, no. 1, 18-28, 2018.
51. K. A. Miles, "How to use CT texture analysis for prognostication of non-small cell lung cancer," *Cancer imaging,* vol. 16, 10, 2016.
52. B. Ganeshan, and K. A. Miles, "Quantifying tumour heterogeneity with CT," *Cancer imaging,* vol. 13, no. 1, pp. 140-149, 2013.
53. M. B. Andersen, S. W. Harders, B. Ganeshan, J. Thygesen, H. H. T. Madsen, F. Rasmussen, "CT texture analysis can help differentiate between malignant and benign lymph nodes in the mediastinum in patients suspected for lung cancer," *Acta Radiologica,* vol. 57, no. 6, pp. 669-676, 2016.
54. S. Wold, K. Esbensen, and P. Geladi, "Principal component analysis," *Chemometrics and Intelligent Laboratory Systems,* vol. 2, no. 1-3, pp. 37-52, 1987.
55. X. Wang, K. Mao, L. Wang, P. Yang, D. Lu, and P. He, "An Appraisal of Lung Nodules Automatic Classification Algorithms for CT Images," *Sensors,* vol. 19, no. 1, 194, 2019.
56. M. Batty, R. Morphet, P. Masucci, and K. Stanilov, "Entropy, complexity, and spatial information," *J Geogr Syst,* vol. 16, pp. 363-385, 2014.
57. E. M. Rikxoort, B. Hoop, S. Vorst, M. Prokop, and B. Ginneken, "Automatic Segmentation of Pulmonary Segments From Volumetric Chest CT Scans," *IEEE Trans. On Medical Imaging,* vol. 28, no. 4, pp. 621-630, 2009.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for identification, segmentation, tracking, and analysis of multiple tumor lesions, the method comprising:
   obtaining a first set of one or more three-dimensional (3D) digital images, wherein at least a portion of the one or more 3D digital images comprises a target organ;
   segmenting the first set of one or more 3D digital images of the target organ into one or more first segment volumes of the target organ;
   identifying and segmenting a first set of a plurality of tumor lesions in each of the one or more first segment volumes of the target organ using a region-growing based segmentation method, wherein the region-growing based segmentation method comprises: i) calculating a first seed point from a predefined second seed point, ii) constructing a priority map for region growing based on the first seed point, and iii) growing a segmentation region using the priority map;
   determining, for each identified tumor lesion in the first set of a plurality of tumor lesions, a 3D location and a segmented volume;
   creating a first 3D spatial distribution of the identified first set of a plurality of tumor lesions, wherein the 3D spatial distribution forms a unique 3D point structure for a patient;
   obtaining a second set of one or more 3D digital images of the target organ at a time after the first set of one or more 3D digital images were obtained;
   segmenting the second set of one or more 3D digital images of target organ into one or more second segment volumes of the target organ;
   identifying and segmenting a second set of a plurality of tumor lesions in each of the one or more second segment volumes of the target organ using the region-growing based segmentation method;
   determining, for each identified tumor lesion in the second set of a plurality of tumor lesions, a 3D location and a segmented volume;
   creating a second 3D spatial distribution of the identified second set of a plurality of tumor lesions;
   co-registering the second 3D spatial distribution of the identified second set of a plurality of tumor lesions with the first 3D spatial distribution of the identified first set of a plurality of tumor lesions to:
      i) identify one or more lesion pairs and calculate a change in volume of the one or more lesion pairs between the first set of a plurality of tumor lesions and the second set of a plurality of tumor lesions,
      ii) determine whether any of the first set of a plurality of tumor lesions are not detected in the second set of a plurality of tumor lesions, and
      iii) determine whether any of the second set of a plurality of tumor lesions were not detected in the first set of a plurality of tumor lesions;
   determining a first total tumor burden for each identified tumor lesion in the first set of the plurality of tumor lesions, wherein the first total tumor burden is a sum of the volume of each identified tumor lesion in the first set of plurality of tumor lesions and determining a second total tumor burden for each identified tumor lesion in the second set of the plurality of tumor lesions wherein the second total tumor burden is a sum of the volume of each identified tumor lesion in the second set of plurality of tumor lesions;
   determining a change in volume from the first total tumor burden to the second total tumor burden;
   determining a growth rate from the change in volume of the first total tumor burden to the second total tumor burden; and
   making a clinical management decision based on: i) the change in volume of each of the one or more lesion pairs, ii) a determination that at least one of the second set of a plurality of tumor lesions was not detected in the first set of a plurality of tumor lesions and is therefore a new lesion, iii) the change in volume of the first total tumor burden to the second total tumor burden, and iv) the growth rate from the change in the first total tumor burden to the second total tumor burden.

2. The method of claim 1, wherein the clinical management decision comprises one of:
   a disease is progressing rapidly and needs immediate intervention;
   progression of the disease is slowing down so the disease is becoming stable;
   a growth rate of lesions that have survived treatment is becoming faster, which is predictive of disease relapse; and
   the disease is in regression.

3. The method of claim 1, further comprising displaying a graphical user interface on a display, said graphical user interface comprised of at least four panels, said four panels including a user control panel, an information panel, and image display panel, and a lesion list panel.

4. The method of claim 1, wherein the method further comprises determining that a lesion was missed and predicting the location of the missed lesion.

5. The method of claim 4, wherein the method further comprises adding back the missed lesion to the image in which the lesion was missed.

6. A system for identification, segmentation, tracking, and analysis of multiple tumor lesions, the system comprising:
   an image capture device;
   a memory; and
   a processor in communication with the memory, wherein the processor executes computer-readable instructions stored in the memory that cause the processor to:
      obtain a first set of one or more three-dimensional (3D) digital image that has been captured by the image capture device, wherein at least a portion of the one or more 3D digital images comprises a target organ;
      segment the first set of one or more 3D digital images of the target organ into one or more first segment volumes of the target organ;
      identify and segment a first set of a plurality of tumor lesions in each of the one or more first segment volumes of the target organ using a region-growing based segmentation method, wherein the region-growing based segmentation method comprises: i) calculating a first seed point from a predefined second seed point, ii) constructing a priority map for region growing based on the first seed point, and iii) growing a segmentation region using the priority map;
      determine, for each identified tumor lesion in the first set of plurality of tumor lesions, a 3D location and a segmented volume; and create a first 3D spatial distribution of the identified first set of plurality of tumor lesions, wherein the 3D spatial distribution forms a unique 3D point structure for a patient;
obtain a second set of one or more 3D digital images of the target organ at a time after the first set of one or more 3D digital images were obtained;
segment the second set of one or more 3D digital images of the target organ into one or more second segment volumes of the target organ;
identify and segment a second set of a plurality of tumor lesions in each of the one or more second segment volumes of the target organ using the region-growing based segmentation method;
determine, for each identified tumor lesion in the second set of plurality of tumor lesions, a 3D location and a segmented volume;
create a second 3D spatial distribution of the identified second set of plurality of tumor lesions;
co-register the second 3D spatial distribution of the identified second set of a plurality of tumor lesions with the first 3D spatial distribution of the identified first set of a plurality of tumor lesions to:
  i) identify one or more lesion pairs and calculate a change in volume of the one or more lesion pairs between the first set of a plurality of tumor lesions and the second set of a plurality of tumor lesions,
  ii) determine whether any of the first set of a plurality of tumor lesions are not detected in the second set of a plurality of tumor lesions, and
  iii) determine whether any of the second set of a plurality of tumor lesions were not detected in the first set of a plurality of tumor lesions;
determine a first total tumor burden for each identified tumor lesion in the first set of the plurality of tumor lesions, wherein the first total tumor burden is a sum of the volume of each identified tumor lesion in the first set of plurality of tumor lesions and determining a second total tumor burden for each identified tumor lesion in the second set of the plurality of tumor lesions wherein the second total tumor burden is a sum of the volume of each identified tumor lesion in the second set of plurality of tumor lesions;
determine a change in volume from the first total tumor burden to the second total tumor burden; and
determine a growth rate from the change in volume of the first total tumor burden to the second total tumor burden, wherein a clinical management decision is made based on: i) the change in volume of each of the one or more lesion pairs, ii) a determination that at least one of the second set of a plurality of tumor lesions was not detected in the first set of a plurality of tumor lesions and is therefore a new lesion, iii) the change in volume of the first total tumor burden to the second total tumor burden, and iv) the growth rate from the change in the first total tumor burden to the second total tumor burden.

7. The system of claim 6, wherein the clinical management decision comprises one of:
a disease is progressing rapidly and needs immediate intervention;
progression of the disease is slowing down so the disease is becoming stable;
a growth rate of lesions that have survived treatment is becoming faster, which is predictive of disease relapse; and
the disease is in regression.

8. The system of claim 6, further comprising a display in communication with the processor, wherein the display displays a graphical user interface comprised of at least four panels, said four panels including a user control panel, an information panel, and image display panel, and a lesion list panel.

9. The system of claim 6, wherein the computer-readable instructions further comprise computer-readable instructions which, when executed by the processor, cause the processor to determine that a lesion was missed and predict the location of the missed legion.

10. The system of claim 9, wherein the computer-readable instructions further comprise computer-readable instructions which, when executed by the processor, cause the processor to add back the missed lesion to the image in which the lesion was missed.

11. A computer program product comprising computer-executable instructions for a method for identification, segmentation, tracking, and analysis of multiple tumor lesions, the computer-executable instructions stored on a non-transitory computer-readable media, said method comprising:
obtaining a first set of one or more three-dimensional (3D) digital images, wherein at least a portion of the one or more 3D digital images comprises a target organ;
segmenting the first set of one or more 3D digital images of the target organ into one or more first segment volumes of the target organ;
identifying and segmenting a first set of a plurality of tumor lesions in each of the one or more first segment volumes of the target organ using a region-growing based segmentation method, wherein the region-growing based segmentation method comprises: i) calculating a first seed point from a predefined second seed point, ii) constructing a priority map for region growing based on the first seed point, and iii) growing a segmentation region using the priority map;
determining, for each identified tumor lesion in the first set of plurality of tumor lesions, a 3D location and a segmented volume;
creating a 3D spatial distribution of the identified first set of plurality of tumor lesions, wherein the 3D spatial distribution forms a unique 3D point structure for a patient;
obtaining a second set of one or more 3D digital images of the target organ at a time after the first set of one or more 3D digital images were obtained;
segmenting the second set one or more 3D digital images target organ into one or more second segment volumes of the target organ;
identifying and segmenting a second set of a plurality of tumor lesions in each of the one or more second segment volumes of the target organ using the region-growing based segmentation method;
determining, for each identified tumor lesion in the second set of plurality of tumor lesions, a 3D location and a segmented volume;
creating a second 3D spatial distribution of the identified second set of plurality of tumor lesions;
co-registering the second 3D spatial distribution of the identified second set of a plurality of tumor lesions with the first 3D spatial distribution of the identified first set of a plurality of tumor lesions to:
  i) identify one or more lesion pairs and calculate a change in volume of the one or more lesion pairs between the first set of a plurality of tumor lesions and the second set of a plurality of tumor lesions, ii) determine whether any of the first set of a plurality of tumor lesions are not detected in the second set of a plurality of tumor lesions, and iii) determine whether any of the second set of a plurality of tumor lesions were not detected in the first set of a plurality of tumor lesions;

determining a first total tumor burden for each identified tumor lesion in the first set of the plurality of tumor lesions, wherein the first total tumor burden is a sum of the volume of each identified tumor lesion in the first set of plurality of tumor lesions and determining a second total tumor burden for each identified tumor lesion in the second set of the plurality of tumor lesions wherein the second total tumor burden is a sum of the volume of each identified tumor lesion in the second set of plurality of tumor lesions;

determining a change in volume from the first total tumor burden to the second total tumor burden; and determining a growth rate from the change in volume of the first total tumor burden to the second total tumor burden, wherein a clinical management decision is made based on: i) the change in volume of each of the one or more lesion pairs, ii) a determination that at least one of the second set of a plurality of tumor lesions was not detected in the first set of a plurality of tumor lesions and is therefore a new lesion, iii) the change in volume of the first total tumor burden to the second total tumor burden, and iv) the growth rate from the change in the first total tumor burden to the second total tumor burden.

12. The computer program product of claim 11, wherein the clinical management decision comprises one of:

a disease is progressing rapidly and needs immediate intervention;

progression of the disease is slowing down so the disease is becoming stable;

a growth rate of lesions that have survived treatment is becoming faster, which is predictive of disease relapse; and the disease is in regression.

13. The computer program product of claim 11, wherein the method further comprises displaying a graphical user interface on a display, said graphical user interface comprised of at least four panels, said four panels including a user control panel, an information panel, and image display panel, and a lesion list panel.

14. The computer program product of claim 11, wherein the method further comprises determining that a lesion was missed and predicting the location of the missed lesion.

15. The computer program product of claim 14, wherein the method further comprises adding back the missed lesion to the image in which the lesion was missed.

* * * * *